US008679307B2

(12) United States Patent
Fischione et al.

(10) Patent No.: US 8,679,307 B2
(45) Date of Patent: Mar. 25, 2014

(54) METHOD AND APPARATUS FOR PREPARING SPECIMENS FOR MICROSCOPY

(75) Inventors: Paul E. Fischione, Export, PA (US);
Alan C. Robins, Horley Surrey (GB);
David W. Smith, Oakmont, PA (US);
Rocco R. Cerchiara, Gibsonia, PA (US);
Joseph M. Matesa, Jr., Murrysville, PA (US)

(73) Assignee: E.A. Fischione Instruments, Inc., Export, PA (US)

( * ) Notice: Subject to any disclaimer, the term of this patent is extended or adjusted under 35 U.S.C. 154(b) by 1551 days.

(21) Appl. No.: 10/633,130

(22) Filed: Aug. 1, 2003

(65) Prior Publication Data
US 2004/0108067 A1    Jun. 10, 2004

Related U.S. Application Data

(60) Provisional application No. 60/400,932, filed on Aug. 2, 2002.

(51) Int. Cl.
*C23C 14/34*    (2006.01)

(52) U.S. Cl.
USPC ............ 204/298.25; 204/298.03; 204/298.06; 204/298.31; 204/298.34; 204/298.36; 118/719; 156/345.31; 156/345.36; 156/345.44

(58) Field of Classification Search
USPC ............ 204/298.06, 298.31, 298.34, 298.36, 204/298.03, 298.25; 156/345.31, 345.38, 156/345.44, 345.36; 118/500, 719
See application file for complete search history.

(56) References Cited

U.S. PATENT DOCUMENTS

| | | | | |
|---|---|---|---|---|
| 3,756,939 | A | * | 9/1973 | Hurwitt .................... 204/298.12 |
| 3,958,124 | A | | 5/1976 | Koch et al. ............... 250/442.11 |
| 4,311,725 | A | * | 1/1982 | Holland .......................... 427/10 |
| 4,595,483 | A | * | 6/1986 | Mahler .................... 204/298.09 |
| 4,858,556 | A | * | 8/1989 | Siebert .......................... 118/664 |
| 5,340,460 | A | * | 8/1994 | Kobayashi et al. ...... 204/298.09 |
| 5,633,502 | A | | 5/1997 | Fischione ................ 250/441.11 |
| 5,783,055 | A | * | 7/1998 | Kamei et al. ............. 204/298.04 |
| 5,922,179 | A | * | 7/1999 | Mitro et al. .............. 204/298.04 |
| 6,039,000 | A | * | 3/2000 | Libby et al. ............... 118/723 E |
| 6,051,113 | A | * | 4/2000 | Moslehi .................... 204/192.12 |
| 6,143,128 | A | * | 11/2000 | Ameen et al. ............ 156/345.24 |

(Continued)

OTHER PUBLICATIONS

Model 682, Precision Etching Coating System (PECS), Gatan Inc., 2001.

(Continued)

*Primary Examiner* — Rodney McDonald
(74) *Attorney, Agent, or Firm* — Metz Lewis Brodman Must O'Keefe

(57) ABSTRACT

An apparatus for preparing specimens for microscopy including equipment for providing two or more of each of the following specimen processing activities under continuous vacuum conditions: plasma cleaning the specimen, ion beam or reactive ion beam etching the specimen, plasma etching the specimen and coating the specimen with a conductive material. Also, an apparatus and method for detecting a position of a surface of the specimen in a processing chamber, wherein the detected position is used to automatically move the specimen to appropriate locations for subsequent processing.

63 Claims, 13 Drawing Sheets

(56) References Cited

U.S. PATENT DOCUMENTS

| | | | |
|---|---|---|---|
| 6,190,062 B1 | 2/2001 | Subramanian et al. | 396/578 |
| 6,203,620 B1 * | 3/2001 | Moslehi | 118/723 R |
| 6,261,406 B1 * | 7/2001 | Jurgensen et al. | 156/345.3 |
| 6,278,203 B1 * | 8/2001 | Novak et al. | 310/12.29 |
| 6,325,857 B1 * | 12/2001 | Miyoshi | 118/724 |
| 6,419,802 B1 * | 7/2002 | Baldwin et al. | 204/192.13 |
| 6,434,814 B1 * | 8/2002 | Chang et al. | 29/603.14 |
| 6,641,703 B2 * | 11/2003 | Nomura et al. | 204/192.12 |
| 6,699,374 B2 * | 3/2004 | Marshall | 204/298.14 |

OTHER PUBLICATIONS

Ion Beam Sputter Deposition and Etching System IBS/e, downloaded from the Internet at http://www.southbaytech.com/cgi-bin/homepage/products/view_product.cfm.

Recent Advances in Broad Ion Beam Techniques/Instrumentation for SEM Specimen Preparation of Semiconductors, Alani R., Mitro, R.J., Hauffe, W., Proceeding from the 25th International Symposium for Testing and Failure Analysis, Nov. 1999.

* cited by examiner

METHOD AND APPARATUS FOR PREPARING SPECIMENS FOR MICROSCOPY

CROSS REFERENCE TO RELATED APPLICATION

This application claims the benefit of U.S. Provisional Application No. 60/400,932 filed on Aug. 2, 2002.

FIELD OF THE INVENTION

The present invention relates to a method and apparatus for preparing specimens for examination in a microscope, such as a scanning electron microscope, and in particular, an apparatus that includes various specimen preparation functionality under continuous vacuum conditions.

BACKGROUND OF THE INVENTION

A scanning electron microscope, or SEM, uses electrons to form an image of a specimen. A beam of electrons is produced in the SEM by an electron gun, e.g., by heating a filament. The electron beam follows a path through the column of the microscope and is focused and directed toward the specimen to be imaged using a series of electromagnetic lenses and apertures. When the electron beam strikes the specimen, a number of signals are generated. The different signals can be used to generate different types of images of the specimen.

One signal comes from what are known as backscattered electrons. This signal is obtained by collecting and analyzing those incident electrons that "bounce" off after interacting with the nuclear and electronic potentials of the atoms of the specimen, substantially back toward their source. Thus, the name backscattered electron. Because these electrons are moving so fast, they can penetrate relatively far into a specimen, and after scattering from sites well below the surface they can escape the specimen. In an SEM, a detector is placed in the path of backscattered electrons, and the resultant signal is used to create an image of the specimen. The abundance and energy of backscattered electrons varies with the specimen's local atomic number. As a result, regions of higher average atomic number appear brighter than those of lower average atomic number elements. Thus, backscattered electrons can be used to get an image that shows the different elements present in the specimen.

Another signal comes from what are known as secondary electrons. A small amount of energy from the incident (beam) electrons couples to the electrons already present in the specimen by electromagnetic interaction. This raises the energy of some specimen electrons to a level that enables them to overcome the specimen's work function, and escape the surface of the specimen with a relatively small kinetic energy, on the order of 5 eV. These electrons are called secondary electrons. Because the energy coupled from the primary beam is small, only specimen electrons that are near the surface of the specimen, typically within 10 nm, can become secondary electrons; specimen electrons from deeper below the surface lose the energy absorbed from the beam before reaching the surface. Thus, images formed by secondary electron detection (SED) can achieve high resolution, as they represent the surface only and not the bulk of the specimen. Secondary electrons are collected by a positively charged detector for production of an image. As is well-known by microscopists, the physical processes involved in SED are highly sensitive to the topography of the specimen. Thus, SED images give contrast according to the surface shape of the specimen, analogous to a conventional photograph of an object illuminated from a point source.

There are several well known techniques used to prepare a specimen prior to examining the specimen in a SEM. Among these techniques are etching, coating and plasma cleaning.

Etching involves the selective removal of a portion or portions of the specimen by one of several processes. Etching can be useful when there is a desire to examine a buried feature of a layered structure such as a microchip. In this case, the top layer or layers can be etched away to expose a buried feature for examination. In addition, as described in more detail below, etching can be used to planarize or smooth out a surface of a specimen, such as the surface of a trench cut into a specimen using a focused ion beam generated, for example, from gallium. In this case, a lower energy ion beam generated from argon can be used to etch and thus planarize the trench surface.

Finally, one important use of etching is in the semiconductor industry, where it is often desired to examine a cross-section of a multi-layer structure made of different materials. When created, however, these cross-sections have little or no topography, and thus cannot be effectively imaged using the secondary electron mode of an SEM. Depending on how the etching process is carried out, different materials will etch selectively, meaning at different rates. By using a selective etching process on a specimen consisting of a cross-section of a multi-layer structure made of different materials, the layers will etch at different rates, resulting in the different layers having different heights. Then, the specimen can be imaged using the secondary electron mode of the SEM, with the topography created by the selective etching providing information on, e.g., the boundaries of each layer in the specimen.

Many etching methods are well known in the art. These methods include ion beam etching, abbreviated IBE, reactive ion beam etching, abbreviated RIBE, chemically assisted ion beam etching, abbreviated CAIBE, and plasma etching, otherwise known as reactive ion etching, abbreviated RIE. As the names suggest, IBE, RIBE and CAIBE all utilize an ion beam in the etching process.

In IBE, an ion beam composed of an inert gas such as argon is generated by an ion beam source, otherwise known as ion gun, and is aimed at a target specimen. The ion beam removes material from the specimen by momentum transfer. In particular, the impinging ions of the ion beam knock atoms out of the target specimen. In IBE, there is a small degree of selectivity, meaning different materials are removed at different rates, because the efficiency of momentum transfer from the ion beam depends on the atomic mass of the target. There is also a high degree of directionality, or anisotropy, because the ions impinge on the specimen from a particular direction. This anisotropy can be used to obtain particular desired results for sample preparation. For example, to produce a smooth, level surface, the ions can be made to impinge on the specimen from a direction nearly parallel to the desired surface. This type of etching is known as planarization and is characterized by having the ion beam impinge on the specimen at lower angles of incidence. Features protruding from the surface will be eroded more quickly than areas in the surrounding plane, and so there is a leveling effect due to the anisotropy. Using IBE for planarization to produce a smooth, level surface is also known as "ion milling." Etching at higher angles of incidence results in topographical enhancement of the specimen because the selectivity of the etching increases as the angle of incidence increases.

In RIBE, a reactive gas, such as $CF_4$, is used by the ion gun to generate the ion beam. As a result, in addition to momentum transfer, a chemical reaction effects the removal of material from the specimen target. The chemical reaction adds a higher degree of selectivity to the process, because different chemical reactions occur with different components of the specimen, and in general these different reactions can have very different rates.

One problem with RIBE is that the reactive ions can also react with the materials of which the ion gun is constructed. This causes corrosion and early wear-out of the gun. CAIBE is somewhat of a hybrid between IBE and RIBE that avoids this problem. In CAIBE, a reactive gas flow, such as iodine, is aimed at the specimen target by a neutral device such as a hose or nozzle. At the same time, an ion beam composed of an inert gas is aimed at the specimen target. The impingement of the ions of ion beam on the surface of the specimen facilitates the chemical reactions caused by the impingement of the reactive gas on the surface of the specimen, thereby providing a more effective selective etch than IBE alone. The problems of RIBE are avoided because the reactive gas is not ionized in the ion gun.

Historically, IBE techniques have been used for Transmission Electron Microscopy (TEM) sample preparation. Due to recent advances in SEM technology, IBE techniques are becoming more applicable for SEM sample preparation. Sample geometry becomes a limitation when trying to adapt IBE technology from TEM to SEM. TEM samples are very consistent in size, whereas SEM samples geometries vary greatly. Many IBE devices are designed to only accommodate the consistent sample size of a TEM sample. When adapting IBE technology to SEM, a system to detect and adjust for variations in sample geometry, or more specifically, the overall height of the sample becomes necessary for practical use of the device.

In plasma etching (RIE), the specimen is exposed to a chemically reactive plasma. Depending on the gaseous species used to generate the plasma, different chemical reactions will be included and selective etching will occur. Many methods are well-known for generating a plasma for plasma etching. One class of plasma etching equipment places the specimen in a gap between two substantially planar, substantially parallel electrodes. Gas is introduced into the gap at a low pressure, for example 1 torr, and the electrodes are connected to the terminals of an alternating voltage source, resulting in an alternating electric field within the gap. The electric field couples energy to electrons of the gas, ionizing some fraction of the gas molecules, thereby forming a plasma within the gap. Because the coupling is primarily electrostatic, this technique is known as "capacitive discharge" plasma. The plasma can contain the original species in the feed-gas, as well as many other combinations of the atoms of the original feed-gas species. The plasma can contain these species as neutral molecules as well as positive- or negative radicals. In the context of etching, any molecule or fragment thereof with a net charge is called an "ion." Ions are accelerated out of the plasma by the electric field of the plasma sheath toward any material surfaces, including the electrodes and the specimen. Neutrals permeate the enclosure by way of diffusion. The ions and/or neutrals can cause a selective etching result because of their greater or lesser disposition to react chemically with the materials of the specimen. In addition, the ions can cause a directional or anisotropic etch result because they are accelerated toward the specimen in a particular direction. These two characteristics taken together make RIE especially useful for introducing topography to cross-sectional samples composed of layers of different materials. The selectivity tends to etch the different materials at different rates, resulting in topographic relief. The anisotropy helps to preserve sharp edges, by reducing the rate of lateral etching, while enhancing the rate of vertical etching. These effects can be enhanced by many techniques including the varying of the relative size of the parallel plates and adding an independent DC source.

Another class of plasma etching equipment uses an alternating electromagnetic field to couple energy to the electrons of a plasma. This is known as inductively coupled plasma, or ICP. The generation of ions and neutral species is similar to that which takes place in the above example. However, the sheath voltage of an ICP is generally much lower than the sheath voltage of a capacitive discharge, and so the ions generally exit the plasma with less speed, resulting in lower anisotropy. In more advanced ICP etchers, the degree of anisotropy can be controlled by adjusting the electrostatic potential of the specimen relative to that of the plasma interior.

Still more similar methods of plasma etching have been developed, particularly for application in semiconductor processing. These methods and the equipment used therefor are known in the field as "dry etching" systems, in contrast to methods and equipment that use acids, for example, which are known as "wet etch" systems.

Since an SEM uses electrons to produce an image, most conventional SEMs require that the samples be electrically conductive. If the specimen is made of a non-conducting insulating material, the impinging electrons of the SEM are not conducted away from the material and will accumulate on the surface of the specimen and cause charging effects that disturb the trajectories of subsequent beam electrons and reduce the quality of the image. In order to image a non-conductive specimen made of an insulating material such as a ceramic or plastic, the specimen must be coated with a thin layer of a conductive material before being imaged in an SEM. Some commonly used conductive materials are carbon, platinum, palladium, gold, gold-palladium, chromium, aluminum and tungsten. The particular conductive material chosen depends on the application. Typically, specimen coating is performed in one of two ways: by thermal evaporation methods or by sputtering methods.

A number of thermal evaporation methods are well known in the art, including resistive heating and electron beam evaporation. In thermal methods, the specimen is placed in a vacuum chamber and evacuated to e.g., $10^{-3}$ to $10^{-5}$ torr, and the coating material to be applied to the specimen is heated within the chamber. In resistive heating methods, the coating material is heated by placing it in contact with an electrical conductor, through which an electrical current is passed, causing heat. Typically, the conductor is in the form of a tungsten boat. In electron beam evaporation methods, electrons are emitted from a filament and accelerated toward the source of coating material to be evaporated. The impact of the electrons impinging on the source material causes heat within the material. By either method, heating the material causes thermal evaporation of the material. The sample to be coated is located so as to experience a flux of the evaporated material on its surface. Because the sample is thermally cool, the evaporated material condenses on its surface and forms a coating.

Several sputtering methods and devices for coating samples are well known in the art. Two such well known methods are ion beam sputtering and magnetron sputtering.

In ion beam sputtering, an ion beam, unusually composed of an inert gas, is aimed at a target consisting of the conductive material. The ion beam removes material as in IBE or ion milling. The specimen is arranged so that some of the removed material will impinge upon it and stick, thereby coating the specimen with a conductive material.

In magnetron sputtering, a magnetically confined, DC plasma is generated that results in a high flux of ions, usually inert, that impinge on the conductive target and remove material by momentum transfer. As in the case of ion beam sputtering, the specimen is arranged so that some of the removed material will impinge on the specimen and stick, forming a coating.

As is well known in the art, a number of parameters involved in the sputtering process control the appearance of the final coating. These parameters include specimen temperature, distance of the specimen from the target, manipulation of the specimen as it is being coated, including rotation, rocking and tilting thereof, target orientation, primary ion energy, vacuum level and target material.

Another essential component of any coating process is the ability to monitor the thickness of the coating material being applied to the specimen surface. The most widely used method uses a crystal oscillator that is placed in the coating chamber near the specimen to be coated. The resonant frequency of the crystal is measured and is a function of how much material has been applied to the surface of the crystal; this in turn can be related through geometry to the quantity of material deposited on the surface of the specimen. The coating process may be automatically controlled such that once a desired thickness of coating material is applied, the coating process is automatically terminated.

One problem that adversely affects the quality of SEM analysis is hydrocarbon contamination of the specimen. This contamination can occur as a result of poor operator handling techniques during the preparation process, such as touching the specimen with an ungloved hand. Other contamination may result from subjecting the specimen to a preparation process that utilizes an oil diffusion pump or a turbomolecular pump backed by a vacuum pump that utilizes oil in its pumping path whereby backstreaming of oil will lead to contamination, the use of hydrocarbon based solvents and adhesives in the preparation process, storage or exposure of the specimen to ambient conditions, and repeated exposure to the SEM vacuum system which may contain oil vapor which has migrated up the electron optics column from a vacuum pump or has entered the chamber through its exposure to ambient conditions. Although contamination of specimens may consist mainly of hydrocarbon compounds, other types of contamination, such as oxides or particulates, can be present. Furthermore, contamination of the specimen surface and of the target can have a detrimental effect on the quality of the coating deposited by a sputtering coating method. Such contamination can lead to adhesion difficulties for the coating material, unevenness of the coating, and possibly the formation of unwanted inter-metallic species. Contamination of the sputtering target can lead to the deposition of unwanted compound materials rather than the monatomic metallic species.

Moreover, a specimen may become contaminated when it is transferred in the ambient environment from one processing device to the next while being prepared for microscopy. For example, a specimen may be so contaminated when transferred from a stand alone plasma cleaning device to a separate stand alone coating or ion milling device.

There are two common cleaning methods that are used in sputtering systems as a quick means of cleaning the specimen. In the first of these methods, used with ion-beam sputtering, the sputtering ion source is re-aimed at the specimen, and the sample is then ion milled for a short period of time. This will knock off unwanted contamination from the surface of the specimen. However, the unwanted contamination is then free to redeposit back onto the specimen or perhaps the sputter-coating target. Furthermore, sputtering of the specimen surface can lead to etching effects. The second of these methods is used in magnetron sputtering systems. In this method, the polarity of the target is reversed so that the ions are accelerated toward the specimen. That is, the roles of target and specimen are reversed. This also may result in etching of the specimen surface, particularly for softer materials.

An alternative cleaning method and solution is described in Fischione, U.S. Pat. No. 5,633,502, entitled "Plasma Processing System for Transmission Electron Microscopy Specimens and Specimen Holders", the disclosure of which is incorporated herein by reference. Fischione discloses a plasma processing method and apparatus in which a low energy RF plasma is preferably used to remove contamination, mainly in the form of hydrocarbons, from specimens. The system comprises a vacuum system, a plasma chamber into which the specimen and the specimen holder are inserted, a housing having an access port with removable inner sleeve components, and a RF power supply which is coupled to the plasma chamber and enables both the generation and maintenance of the plasma. To commence processing, the vacuum system is engaged for the evacuation of the plasma chamber for subsequent formation of the plasma. Plasma formation is preferably initiated through the coupling of an oscillating field to the plasma chamber. Many process gas mixtures can be used, including a mixture of a noble gas and an oxidant. A 25% oxygen and 75% argon mixture is preferred. The oxygen chemically reacts with carbonaceous substances on the specimen and converts them to volatile species such as $CO$, $CO_2$ and $H_2O$. The argon dilutes the oxygen and thereby simplifies safety issues in gas handling.

SUMMARY

The preferred embodiment of the present invention relates to an apparatus for preparing a specimen for microscopy including a vacuum chamber, a plasma generator connected to the vacuum chamber for plasma cleaning the specimen, an ion source connected to the vacuum chamber for etching the specimen, a plasma etching assembly connected to the vacuum chamber for plasma etching the specimen and an assembly for coating the specimen with a conductive material. The plasma cleaning, etching, plasma etching and coating of the specimen may be performed within the vacuum chamber under continuous vacuum conditions that are established therein. The plasma generator may include a plasma tube, a coil wrapped around the plasma tube, and an RF power supply connected to the coil. The apparatus may further include a source of process gas connected to the plasma tube which may include oxygen or oxygen mixed with a non-reactive gas such as argon. The apparatus may be adapted to perform ion beam etching or reactive ion beam etching, depending on the gas fed to the ion source. In a most preferred embodiment, the plasma etching is performed utilizing a plasma generated by capacitive discharge techniques wherein the plasma is generated by an electric field that is generated within a gap between two electrodes. The coating in the most preferred embodiment is performed using ion beam sputter coating techniques where an ion beam is directed at a target formed of a conductive material. The apparatus may include a lever supported by the vacuum chamber for holding the target wherein the lever is selectively moveable into a position in which the ion beam is directed at the target. Furthermore, the apparatus may include a plurality of targets, wherein the ion beam is directed at a selected one of the targets. The apparatus may further include a moveable sample stage for holding the specimen, wherein the sample stage is moveable to a plurality of processing positions inside the vacuum chamber. In one embodiment, the sample stage is moveable in a first direction along a vertical axis of the vacuum chamber, and the apparatus includes components for detecting a position of a surface of the specimen along the vertical axis. Once this position is detected, the sample stage may be moved automatically to the plurality of processing positions based on this detected position. The components for detecting this height may, in one specific embodiment, include a laser beam or other beam, wave or charged particle generator and a sensor, both supported by the vacuum chamber. The sample stage is most preferably adapted to have four or more degrees of independent selective motion, such as rotation about the vertical axis, the ability to tilt in two directions, and the ability to move vertically.

The present invention also relates to a method for preparing a specimen for microscopy including determining a first position of a surface of the specimen along an axis of a processing chamber and automatically moving the specimen to one or more processing locations within the processing chamber based on the first position. According to a specific embodiment, the determining step includes generating a beam, directing the beam at a sensor, moving the specimen along the axis, and establishing the first position when a predetermined level is measured by the sensor. The predetermined level may, in one specific embodiment, be a level equal to approximately 50% of a level measured when the sensor is completely unobscured. The present invention also relates to an apparatus for performing this method.

According to an alternate embodiment, the present invention relates to an apparatus for preparing a specimen for microscopy including a plasma generator for plasma cleaning the specimen and an assembly for coating the specimen with a conductive material, wherein the plasma cleaning of the specimen and the coating of the specimen may be performed under continuous vacuum conditions. The apparatus may further include equipment for removing material, such as by etching, from the specimen under the continuous vacuum conditions. This equipment may include an ion source for directing an ion beam at the specimen. In one specific embodiment, the equipment for coating the specimen includes a magnetron sputtering device. In yet another embodiment, the equipment for coating the specimen includes an ion source for directing an ion beam at a target formed of a conductive material. The apparatus may include a single chamber or may include first and second chambers connected through a vacuum valve. The apparatus may further include a source of process gas positioned adjacent the ion source for performing chemically assisted ion beam etching.

In yet another alternative embodiment, the present invention relates to an apparatus for preparing a specimen for microscopy including a plasma generator for plasma cleaning the specimen, and an assembly for removing material from the specimen, such as by etching, wherein the plasma cleaning of the specimen and the removing of material from the specimen may be performed under continuous vacuum conditions. The assembly for removing the material such as by etching may comprise an ion source for directing an ion beam at the specimen. The apparatus may include a single chamber for processing the specimen or may include first and second chambers connected to one another through a vacuum valve. The apparatus may further include a specimen stage for holding the specimen that is tiltable and rotatable.

In yet a further embodiment, the present invention relates to an apparatus for preparing a specimen for microscopy including an assembly for coating the specimen with a conductive material and an assembly for plasma etching the specimen, wherein the coating of the specimen and the plasma etching of the specimen may be performed under continuous vacuum conditions. The plasma etching may be performed using capacitive discharge plasma etching techniques, wherein the apparatus further includes first and second electrodes defining a gap therebetween for receiving the specimen and an alternating voltage source connected to the first and second electrodes for generating an electric field within the gap, which electric field generates a plasma from a gas introduced into the gap. The apparatus may further include a specimen stage for holding the specimen, wherein at least a portion of the specimen stage is one of the electrodes used in the plasma etching. The plasma etching may also, in the alternative, be performed using inductively coupled plasma etching techniques. The coating assembly may, in one specific embodiment, include a magnetron sputtering device. In another embodiment, the coating assembly may include an ion source for directing an ion beam at a target formed of a conductive material. The apparatus may further include an assembly for ion beam etching the specimen, wherein the ion beam etching is also performed under the continuous vacuum conditions. The apparatus may include a single chamber for processing the specimen under the continuous vacuum conditions. The apparatus may further include a plasma generator for plasma cleaning the specimen also under the continuous vacuum conditions.

According to still a further embodiment, the present invention relates to an apparatus for preparing a specimen for microscopy including a first vacuum chamber, a second vacuum chamber connected to the first vacuum chamber, a specimen stage moveable between a first position and a second position under continuous vacuum conditions, the first position being inside the first vacuum chamber and the second position being inside the second vacuum chamber, an assembly for coating the specimen with a conductive material supported by the first vacuum chamber, and an assembly for plasma etching the specimen, at least a portion of which is supported by the second vacuum chamber. The plasma etching may utilize capacitive discharge plasma etching techniques wherein the plasma etching assembly includes first and second electrodes defining a gap therebetween and an alternating voltage source connected to the first and second electrodes for generating an electric field within the gap, the electric field generating a plasma from a gas introduced into the gap. A portion of the specimen stage may act as one of the electrodes. The coating assembly may include a magnetron sputtering device, or, alternatively, may include an ion source for directing an ion beam at a target formed of a conductive material. The apparatus may also include an ion source for directing an ion beam at the specimen for ion beam etching the specimen under the continuous vacuum conditions. In addition, the apparatus may include a plasma generator for plasma cleaning the specimen under the continuous vacuum conditions.

BRIEF DESCRIPTION OF THE DRAWINGS

Further features and advantages of the present invention will be apparent upon consideration of the following detailed description of the present invention, taken in conjunction with the following drawings, in which like reference characters refer to like parts, and in which.

DESCRIPTION OF THE PREFERRED EMBODIMENTS

Figure 1:
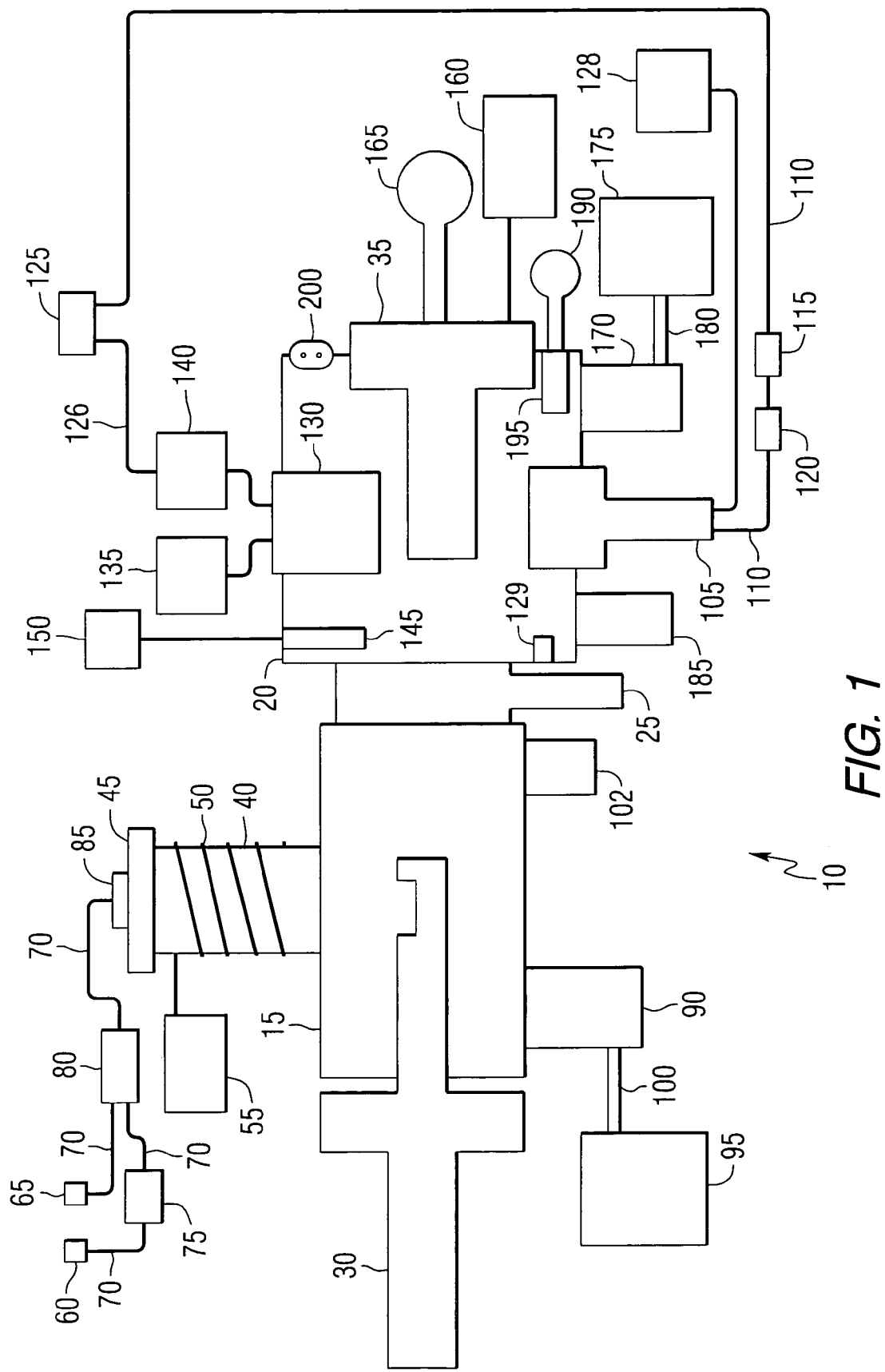
FIG. 1 is a schematic diagram of a first embodiment of an apparatus for preparing specimens for microscopy according to the present invention.

Referring to FIG. 1, a block diagram of plasma cleaning, etching and coating apparatus 10 according to a first embodiment of the present invention is shown in which specimens may be plasma cleaned, etched or coated alone or in any combination under a continuous vacuum state. Plasma cleaning, etching and coating apparatus 10 includes plasma chamber 15 made of, for example, stainless steel or aluminum, in which a specimen may be subjected to a plasma cleaning operation such as that described in Fischione, U.S. Pat. No. 5,633,502. Plasma cleaning, etching and coating apparatus 10 also includes etching and coating chamber 20 made of, for example, stainless steel or aluminum, in which a specimen may be etched, coated, or both. Plasma chamber 15 and etching and coating chamber 20 are connected by vacuum valve 25, which may be manually or automatically actuated. Preferably, vacuum valve 25 is provided with interlocking capability to prevent inadvertent opening of vacuum valve 25 if plasma chamber 15 and etching and coating chamber 20 are at unequal pressures, such as where one is at atmospheric pressure while the other is under vacuum conditions.

Figure 3:
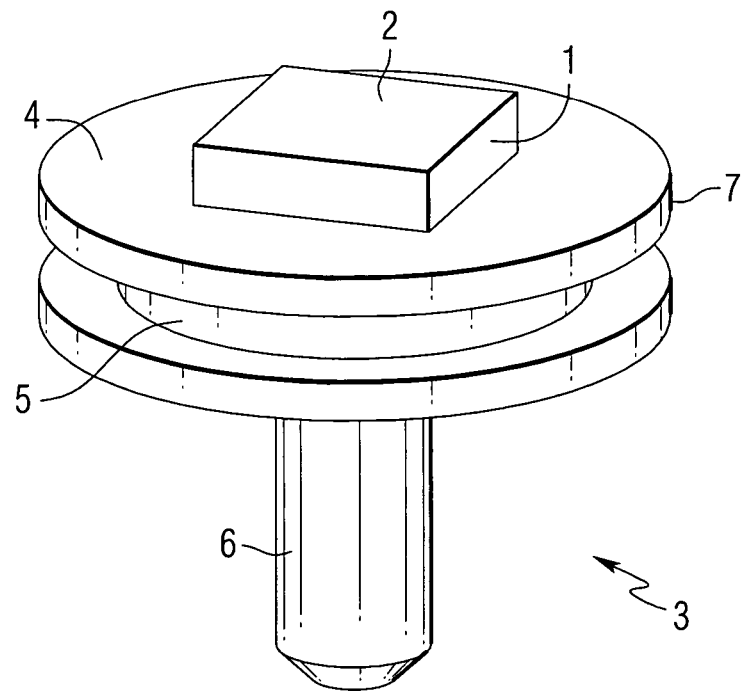
FIG. 3 is an isometric view of a prior art stub mounted specimen.

Referring to FIG. 3, a stub-mounted specimen 3 is shown. A specimen 1 to be prepared for scanning electron microscopy is mounted to a standard specimen stub 7 using an adhesive, mechanical clamping, or the like. Several standard specimen stubs of varying size are commercially available and generally comprise a flat top platform 4, for holding the specimen 1. Some commercial specimen stubs also include a downwardly extending pin 6, while other do not. Such commercially available specimen stubs vary in height from 5-20 mm and in diameter from 12.5-50 mm. Specimen stubs are available from distributors such as Ted Pella Inc. Preferably, specimen stubs 7 incorporating an annular groove 5 are used to provide a geometric feature to facilitate gripping and manipulation. The specimen 1 is mounted to the stub 7 preferably with the surface to be prepared 2 situated parallel to the flat top platform 4.

Figure 2:
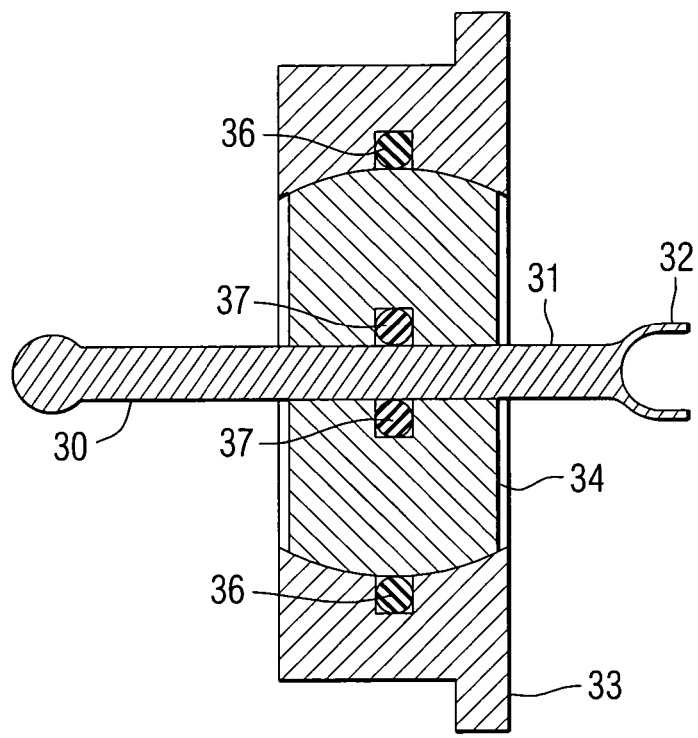
FIG. 2 is a diagram, partially in cross section, of a transfer rod used to move a stub mounted specimen as shown in FIG. 3 inside of a vacuum vessel.

FIG. 2 shows a transfer rod 30, which is used to move a stub-mounted specimen 3 inside a vacuum. The transfer rod 30 has a gripper 32 that is capable of holding one or more stub-mounted specimens 3 shown in FIG. 3. Gripper 32 shown in FIG. 2 has a fork-like structure that can mate with the groove 5 in the stub-mounted specimen 3 of FIG. 3. Gripper 32 is affixed to the end of a smooth shaft 31 that provides a linear-motion, vacuum feed-through by way of sliding seal 37 in spherical flange 34. Spherical flange 34 provides vacuum feedthrough of mechanical rotation by way of sliding seal 36 in vacuum flange 33. By a combination of the motions afforded by sliding seals 36 and 37, the stub-mounted specimen 3 can be maneuvered to various positions inside vacuum chambers 15 and 20 by an operator external to the vacuum.

Referring again to FIG. 1, plasma cleaning, etching and coating apparatus 10 is provided with transfer rod 30 including a gripper 32 that accommodates one or more stub-mounted specimens 3. Transfer rod 30 enables stub-mounted specimens 3 held in gripper 32 to be moved back and forth between plasma chamber 15 and etching and coating chamber 20 through vacuum valve 25 while both plasma chamber 15 and etching and coating chamber 20 are under vacuum conditions as are generally suitable for their respective processes in accordance with established art. In order to allow for such movement, transfer rod 30 must be of sufficient length to reach from plasma chamber 15 to etching and coating chamber 20. The specimen stage 35 contained within etching and coating chamber 20 has a hole that can accept the pin 6 of the stub-mounted specimen 3. By a combination of movements of shaft 31 within spherical flange 34 and of spherical flange 34 within flange 33, stub-mounted specimen 3 can be placed onto specimen stage 35, and the gripper 32 withdrawn and detached from stub-mounted specimen 3, leaving stub-mounted specimen 3 separated from transfer rod 30 and deposited onto specimen stage 35. By another combination of movements of transfer rod 30, gripper 32 can engage stub-mounted specimen 3 and lift it out of specimen stage 35, subsequently moving stub-mounted specimen 3 to various other positions within chambers 15 and 20. It will be appreciated by those of skill in the art that configurations other than the pin-and-hole, or fork-and-groove, can be used for gripping and transfer of the stub-mounted specimen 3. For example, bayonet connections, screw threads, dovetails, and magnets could also be used. The present embodiment is preferred because of its simplicity and its compatibility with readily-available specimen stubs 7 having grooves on their perimeters.

Transfer rod 30 is attached to plasma chamber 15 by way of a flange 33 and a mating flange (not shown) on plasma chamber 15, so as to form a vacuum-tight seal with plasma chamber 15. The connection between transfer rod 30 and plasma chamber 15 is preferably a detachable one, using, for example, the well known ISO "KF" style design. A stub-mounted specimen can be introduced into plasma chamber 15 by venting plasma chamber 15 to atmospheric pressure, detaching transfer rod 30 from plasma chamber 15, affixing the stub-mounted specimen to the gripper 32 of transfer rod 30, and re-attaching transfer rod 30 to plasma chamber 15.

Plasma tube 40 is connected to plasma chamber 15. Plasma tube 40 is preferably a hollow, cylindrical tube made of quartz. Quartz is preferred due to its low conductivity and permeability, which allow an alternating electromagnetic field to pass through it substantially unattenuated. Other suitable materials for plasma tube 40 include glass. Plasma tube 40 is capped by flange 45. Coil 50 is wrapped around the exterior of plasma tube 40, and is connected to RF power supply 55. Gas inlet fitting 85 is located at the end of plasma tube 40 opposite plasma chamber 15. Process gas inlet 60 is provided as a connection to a source of process gas (not shown), and vent gas inlet 65 is provided as a connection to a source of vent gas (not shown), such as argon, for venting purposes. Mass flow controller 75 is connected to process gas inlet 60 by tubing 70, which is preferably constructed of stainless steel, although other materials such as viton, reinforced plastic, copper and polyethylene may be used. Mass flow controller 75 regulates the flow of process gas into plasma tube 40 during cleaning operations. As an alternative to mass flow controller 75, a manual metering valve may be used. Valve 80, such as a 3-way valve, is used to switch between a state in which plasma tube 40 is vented to atmospheric pressure and a state in which the process gas is permitted to flow through tubing 70 and gas inlet fitting 85 and into plasma tube 40.

Also coupled to plasma chamber 15 is turbo pump 90. Turbo pump 90 provides a suitable vacuum level in plasma tube 40 and plasma chamber 15 for the generation and maintenance of the plasma, preferably on the order of $10^{-2}$ torr with process gas flowing, and $10^{-6}$ torr with the gas sources turned off. Turbo pump 90 will not operate properly unless its outlet is pre-pumped. Thus, oil-free diaphragm pump 95 is connected to turbo pump 90 by tubing 100 for purposes of reducing the foreline or outlet pressure of turbo pump 90. An oil-free system, also known as a dry system, is preferred to eliminate the possibility of introducing hydrocarbon contamination into plasma chamber 15. Such oil-free or dry systems are characterized by (i) not having oil or other natural or synthetic fluid lubricants in the pumping path, or (ii) not being oil or natural or synthetic fluid lubricant sealed, wherein oil or another natural or synthetic fluid lubricant forms a seal of the vacuum chamber of a pump in the vacuum system. Other types of oil-free or dry pumps that may be substituted for oil-free diaphragm pump 95 include molecular drag pumps, turbomolecular drag pumps, molecular drag pumps backed by a diaphragm pump, turbomolecular drag pumps backed by a diaphragm pump, cryosorption pumps, reciprocating piston pumps, scroll pumps, screw pumps, claw pumps, non-oil sealed single and multistage piston pumps, and rotary lobe (Roots) pumps. Vacuum gauge 102 is provided to monitor the vacuum level in plasma chamber 15 and plasma tube 40.

Plasma is initiated in plasma tube 40 through the inductive coupling of an oscillating electromagnetic field to plasma tube 40 into which the process gas flows. RF power supply 55 and coil 50 provide the oscillating field that is used to generate the plasma. Generation of a plasma by inductive coupling of an oscillating electromagnetic field is commonly referred to as ICP. The plasma, once generated, flows into plasma chamber 15 by diffusion and cleans a specimen or specimens loaded onto transfer rod 30.

For effective RF power generation, the power circuitry should be matched to plasma tube 40 and coil 50 in terms of impedance in order to minimize reflected power. By minimizing the reflected power, overall electrical efficiency is increased. In virtually all cases, matching networks are included as integral components of RF power supply 55.

The preferred frequency to be used by RF power supply 55 is 13.56 mHz. This frequency is an industrial frequency set aside by the FCC for applications similar to the one described herein and is commonly employed in industrial plasma generation. The frequency, however, of RF power supply 55 is not limited thereto, but may be classified as high frequency at any frequency greater than 60 Hz.

For general applications, a process gas consisting of a mixture of 25% oxygen and 75% argon or some other non-reactive gas such as nitrogen is preferred. Oxygen and its radicals chemically react with the hydrocarbon contamination on the specimen and converts it to volatile species such as $CO$, $CO_2$ and $H_2O$, which are evacuated by turbo pump 90 and diaphragm pump 95. The non-reactive gas such as argon dilutes the oxygen in the process gas to a level that simplifies safe handling. A process gas consisting solely of oxygen may also be used. Such a process gas will result in faster processing than the oxygen and non-reactive gas mixture. Also, other reactive gases, such as iodine, chlorine and $CF_4$, may be used as the process gas, or components thereof, and should be chosen depending upon the material to be processed and the contaminant to be removed.

Plasma Chamber 15 and plasma tube 40 employ a non-equilibrium high frequency plasma in which the electron temperature is high, for example 10,000K, but the ion and neutral temperature is low, for example 500K. Use of such a plasma for processing increases the temperature of the material being processed typically to only a few degrees above ambient temperature. The fact that the processing is effected without any significant heating of the specimen or specimens is preferable because excessive heating of the specimen or specimens may alter the properties of the material.

Although a particular type of plasma generator for plasma cleaning a specimen is shown in FIG. 1, it will be appended that alternate plasma generators may also be used, including, but not limited to, capacitive discharge plasma generators, electron-cyclotron resonance plasma sources, DC charges, or any other known device for generating a suitable plasma.

Etching and coating chamber 20 is provided with magnetron sputtering head 105 for coating a specimen or specimens with a desired material while inside etching and coating chamber 20. Several suitable magnetron sputtering heads with simple vacuum interfaces are commercially available. One example of a suitable magnetron sputtering head is the ONYX-1 sold by Angstrom Sciences located in Duquesne, Pa. The target, i.e., the material to be sputtered onto the specimen or specimens, is internal to magnetron sputtering head 105. In magnetron sputtering head 105, a plasma is formed between the target and the specimen or specimens to be coated. The plasma removes material from the target and deposits it onto the specimen or specimens. Gas for magnetron sputtering head 105 is supplied through high purity gas line 110, such as one made of stainless steel tubing to minimize contamination, and is regulated by needle valve 115. Solenoid valve 120 is provided in gas line 110 and is used to switch gas flow on and off. A suitable gas for use in magnetron sputtering head 105 is argon, although other gasses such as neon or xenon may be used. The gas is supplied from a source (not shown) such as a compressed-gas cylinder through gas inlet 125. Power supply 128 is coupled to magnetron sputtering head 105 and is preferably a current-regulated, 1000-volt DC source. Typical operating pressures for magnetron sputtering head 105 are between 0.5 and 50 millitorr. Crystal oscillator 129 is provided in etching and coating chamber 20 to measure the amount of coating material deposited on the surface of the specimen or specimens.

The diameter of the target in magnetron sputtering head 105 is preferably approximately 1 or 2 inches to allow for a specimen coating area of up to approximately 1.5 inches. In addition, the distance between magnetron sputtering head 105 and the specimen or specimens to be coated is preferably between 2 and 6 inches. To facilitate operation at the preferred distances, magnetron sputtering head 105 may be provided with a variable height adjustment using for example a sliding O-ring seal. Alternatively, the height of specimen stage 35 may be variable.

As an alternative to magnetron sputtering head 105, other types of equipment for depositing coatings on specimens, such as those described elsewhere herein, may also be used, including, but not limited to, ion beam sputter coaters and evaporators.

Etching and coating chamber 20 is also provided with ion gun 130 for etching a specimen or specimens inside etching and coating chamber 20 using ion beam etching. Ion gun 130 generates a beam of ions and accelerates them to the specimen or specimens placed in specimen stage 35. The impingement of the charged ions on the specimen or specimens removes specimen material as a result of momentum transfer. Ion gun 130 generates the beam of ions by creating an initial plasma and extracting the ions from the plasma. The plasma can be created by a DC or RF field, or by electron impact. In addition, ion gun 130 may include a filament, or may be filament-less. A filament-less ion gun that generates the plasma using DC is preferred because such an ion gun produces a broad-beam, high current density ion beam capable of fast etching rates over large areas, and allows for long running times since there is no need to change a filament. Also, filament-less ion guns are superior to filamented guns in terms of compatibility with reactive process-gas species, since the high filament surface temperatures promote fast reactions, leading to rapid corrosion of filaments. A suitable filament-less, DC ion gun is the Hollow-anode discharge source included in the Model 1010 Ion Mill sold by E.A. Fischione Instruments located in Export, Pa. Although ion gun 130 is preferably a filament-less, DC ion gun, it should be noted that ion gun 130 may also be of the filament type or may use RF to generate the plasma. Examples of suitable filament type and RF based ion guns are sold by Kimball Physics located in Wilton, N.H. and by Oxford Applied Research located in Oxfordshire, United Kingdom.

Ion gun 130 will preferably have a beam diameter of approximately 1-20 mm at specimen stage 35 according to the extent of the area to be etched, and a maximum current density of 1 $mA/cm^2$ to provide rapid etching. In addition, the energy of ion gun 130 is preferably in the range of 50-6000 eV. Higher energies give faster etching but produce more surface damage to the specimen, whereas lower energies produce less surface damage but require longer etching times.

Coupled to ion gun 130 is power supply 135. A suitable example of power supply 135 for use with DC based ion guns is the 2A24-P125 sold by Ultravolt Inc. located in Ronkonkoma, N.Y. Suitable examples of power supply 135 for use with RF based ion guns are sold by Advanced Energy located in Fort Collins, Colo. Process gas, such as argon or xenon, is supplied to ion gun 130 from a source (not shown) such as a compressed gas cylinder through gas inlet 125 and gas line 126, such as stainless steel tubing. Mass flow controller 140 is provided in gas line 126 and regulates the flow of the process gas, such as by using well known feedback loop control techniques.

To allow for chemically assisted ion etching with reactive gases, such as iodine and iodine mixtures, etching and coating chamber 20 may be provided with gas inlet orifice 145 positioned near the path of the ions from ion gun 130. Gas inlet orifice 145 is coupled to source 150 of process gas. The accelerated ions from ion gun 130 collide with the process gas and form reactive species, which then diffuse or otherwise migrate towards specimen stage 35. The reactive species will chemically react with the specimen or specimens and remove certain materials faster than others, providing a more pronounced selective etch than if solely an inert gas such as argon is used. The process gas can in general also react with the specimen directly, without action of the ion beam, or can be broken by the ion beam into reactive species after adsorption onto the surface of the specimen. If chemically assisted ion etching is to be utilized, the materials used for etching and coating chamber 20 and the other components continued therein are preferably chosen to be compatible with corrosive and reactive gases.

Other types of equipment for removing material from the specimen may be used as an alternative to ion gun 130, including, but not limited to, equipment for reactive ion etching or plasma etching specimens, which are described in more detail elsewhere herein.

Specimen stage 35 is provided in etching and coating chamber 20 to hold the specimen or specimens during the coating and etching processes. Specimen stage 35 is preferably adapted to hold standard commercially available specimen stubs of varying sizes. According to a preferred embodiment of the present invention, specimen stage 35 is adapted to be selectively tilted with respect to ion gun 130 over a range of 0 to 90 degrees. The tilting capacity enables the incident angle of the ion beam to be varied from parallel to the specimen surface, resulting in mostly planarization of the surface, to normal to the specimen surface, resulting in the most selective etching. In addition, specimen stage 35 is preferably adapted to be selectively rotated in the plane of the specimen surface. Rotational motion in the plane of the specimen surface is known to improve the quality of planarization for many types of specimens. Titling and rotating specimen stage 35 during the coating process yields a more even surface coating of the specimen. Tilting and rotating of specimen stage 35 is controlled by conventional mechanical manipulators, including components such as stepper motors, gears, bearings, shafts, etc., shown at 160 in FIG. 1.

As is known in the art, specimen stage 35 is preferably cooled during the etching process to minimize artifacts. For this purpose, liquid nitrogen dewar 165 is attached to specimen stage 35 to provide conductive cooling of specimen stage 35. Specimen stage 35 may be provided with a heater, for example of the resistive type, to rapidly elevate its temperature prior to venting the chamber or to removal of the specimen from the system into atmosphere, where water vapor and other vapors are present and could condense on a cold specimen.

Turbo pump 170, backed by diaphragm pump 175 through connecting tube 180, is coupled to etching and coating chamber 20. Turbo pump 170 provides suitable vacuum levels in etching and coating chamber 20 for the etching and coating processes, for example on the order of $10^{-4}$ to $10^{-7}$ torr. Vacuum gauge 185 is provided to monitor the vacuum level within etching and coating chamber 20.

Magnetron sputtering head 105 and ion gun 130 may require cooling during operation. For this purpose, etching and coating chamber 20 is provided with tubing and fittings (not shown) to allow for magnetron sputtering head 105 and ion gun 130 to be water-cooled.

Etching and coating chamber 20 is provided with a cold trap for cryo-trapping of water vapor and other residual volatile species, comprising liquid nitrogen dewar 190 attached to etching and coating chamber 20 and conduction cooled cold baffle 195 inside etching and coating chamber 20. Conduction components are preferably made of copper to provide a temperature less than −140° C. at cold baffle 195. A hold time of 4-8 hours is preferred for user convenience.

Etching and coating chamber 20 preferably includes viewing window 200. Preferably, viewing window 200 is oriented with respect to specimen stage 35 to minimize reflections from room lighting, and most preferably includes and anti-reflective coating.

Etching and coating chamber 20 may be provided with a magnifying optical viewing system (not shown) comprising a light microscope or a CCD camera mounted external to viewing window 200. Preferably, the viewing system would yield a magnification in excess of 1000×. Depending on the size of etching and coating chamber, a long focal distance objective is required. A high intensity light source is preferably provided for good illumination of the specimen or specimens, with the light source preferably being mounted inside the etching and coating chamber 20 to avoid reflection from viewing window 200.

Moveable shutters or baffles (not shown) are preferably positioned in front of the viewing window 200 and magnetron sputtering head 105 to protect them from deposition of foreign material when not in use. For example, the shutter over the magnetron sputtering head 105 prevents deposition of etching products from ion beam etching onto the magnetron target surface; these products could otherwise be deposited onto the specimen during subsequent magnetron sputter coating. Similarly, the shutter over the viewing window 200 prevents deposition of etching and/or coating products on the viewing window; these products would otherwise interfere with the optical clarity of the window 200.

In operation, a user switches on the power to plasma cleaning, etching and coating apparatus 10 and initiates the vacuum in the etching and coating chamber 20. This is allowed to reach a level below, for example, $3.75 \times 10^{-6}$ torr. At the same time, specimen stage 35 and cold baffle 195 are cooled by introducing liquid nitrogen into liquid nitrogen dewars 165 and 190. The specimen or specimens that have been mounted onto specimen stubs are loaded on the gripper 32, which is located at the end of transfer rod 30. This requires plasma cleaning chamber 15 and plasma tube 40 to be vented and transfer rod 30, holding the gripper 32 and stub-mounted specimen 3, to be introduced into plasma cleaning chamber 15. Plasma cleaning chamber 15 and plasma tube 40 are then evacuated to a baseline pressure of $10^{-6}$ torr, for example, by turbo pump 90. Plasma cleaning of the specimen or specimens is then initiated by allowing the process gas to flow into plasma tube 40 from process gas inlet 60 through mass flow controller 75 and valves 80. The plasma is initiated in plasma tube 40 by inductively coupling the RF field created by coil 50 and RF power supply 55 to plasma tube 40. The plasma migrates from plasma tube 40 into plasma chamber 15 and cleans the specimen or specimens contained therein on transfer rod 30. Once plasma cleaning is complete, process gas flow is terminated and the plasma cleaning chamber 15 is allowed to evacuate to baseline pressure. Etching and coating chamber 20 is at or near its base pressure of, for example $10^{-7}$ torr. Vacuum valve 25 is opened and transfer rod 30 is pushed into etching and coating chamber 20 until the gripper 32 is positioned in etching and coating chamber 20 and the specimen stub or stubs 7 engage specimen stage 35. Once the specimen stub 7 engages specimen stage 35, the gripper 32 on the end of transfer rod 30 releases the stub 7 and is retracted with transfer rod 30 through vacuum valve 25 and vacuum valve 25 is closed. Specimen stage 35 is tilted to the desired etching angle and rotation of specimen stage 35 optionally commences. The specimen or specimens are etched in etching and coating chamber 20 for the desired time, either through ion beam etching or chemically assisted ion beam etching using ion gun 130. Once etching is complete, specimen stage 35 is returned to its initial exchange position and the process gas flow is stopped. Etching effluents are evacuated by turbo pump 170. If additional plasma cleaning is desired at this point, vacuum valve 25 is opened and transfer rod 30 is used to pick up the specimen stub 7. Transfer rod 30, having picked up the specimen stub 7, is retracted through vacuum valve 25 into plasma cleaning chamber 15 where the specimen or specimens may once again be plasma cleaned. Once plasma cleaning has been completed, vacuum valve 25 is once again opened and transfer rod 30 is moved into etching and coating chamber 20 and the specimen stub 7 is placed onto specimen stage 35. The transfer rod 30 is retracted through vacuum valve 25 and vacuum valve 25 is closed. The high vacuum in etching and coating chamber 20 is allowed to reach its base pressure or nearly so, in order to rid the chamber of possible contaminants such as water vapor. With the shutter in position in front of magnetron sputtering head 105, a pre-sputtering step may be performed to remove the oxide layer from certain targets, such as chromium or tungsten targets. Alternatively, this pre-sputtering step can be eliminated. Once any pre-sputtering is complete, the shutter is moved from the location in front of magnetron sputtering head 105 and magnetron sputtering head 105 begins coating the specimen or specimens for the desired time, depending upon the desired coating thickness, as measured by crystal oscillator 129. Once the desired coating has been completed, gas flow is stopped and magnetron sputtering head 105 is de-energized. Once the vacuum has recovered to its base pressure or nearly so, vacuum valve 25 is opened and the specimen stub is recovered using transfer rod 30. Transfer rod 30 is then retracted into plasma cleaning chamber 15 through vacuum valve 25 and vacuum valve 25 is closed. If desired, an additional plasma cleaning step may then be performed in plasma cleaning chamber 15. Once completed, plasma cleaning chamber 15 is vented to atmospheric pressure and transfer rod 30 is removed from plasma cleaning chamber 15. The specimen stubs holding the specimens may then be transferred to the scanning electron microscope for analysis.

Figure 4:
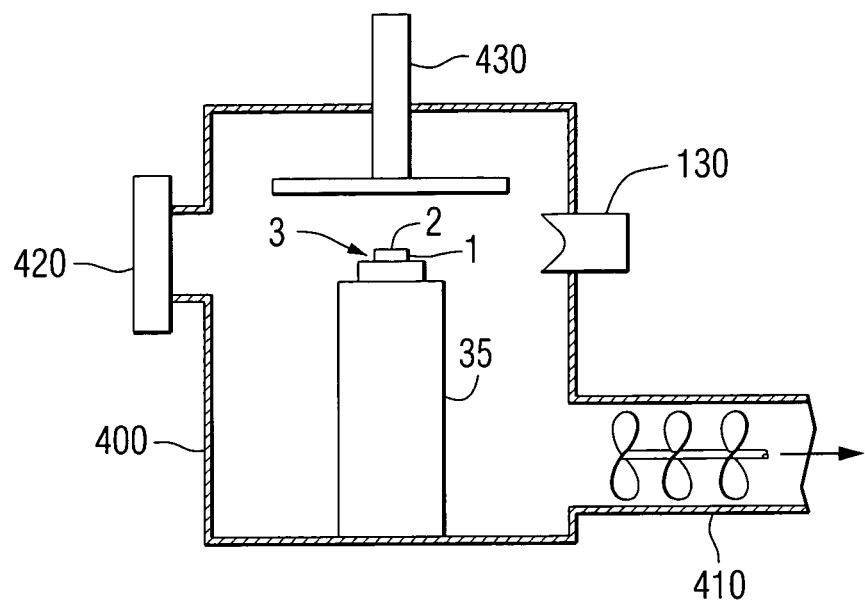
FIG. 4 is a schematic diagram of a second embodiment of an apparatus for preparing specimens for microscopy according to the present invention.

In another embodiment of the present invention, shown schematically in FIG. 4, the apparatus includes one vacuum vessel 400 having a vacuum pump 410, such as a turbo pump 90 backed by diagram pump 95 shown in FIG. 1, a port 420 for inserting and extracting specimens, an ion gun 130 for ion beam etching, and an electrode system for performing RIE. FIG. 4 shows one RIE electrode as a moveable plate 430 and the other RIE electrode as a stub-mounted specimen 3. Not shown in FIG. 4 are a source of alternating voltage between moveable plate 430 and stub-mounted specimen 3, and a source of process gas into vacuum vessel 400 to provide suitable pressure of for example, 1 torr of suitable process gas, for example carbon tetraflouride ($CF_4$), for RIE. It is noted that other electrode configurations are possible. For example, moveable plate 430 could be omitted and the walls of vacuum vessel 400 could be used as a substitute. However, moveable plate 430 is preferred to allow physical adjustment of the gap in which the RIE plasma forms. In this embodiment, the method comprises introducing a specimen 1 or preferably a stub-mounted specimen 3 into the vacuum vessel 400, through port 420. The stub-mounted specimen 3 is held by specimen stage 35, which preferably includes well-known manipulators for tilting stub-mounted specimen 3 relative to ion gun 130 and rotating stub-mounted specimen 3 about an axis approximately normal to the surface 2 of specimen 1 to be prepared, shown in FIG. 3. Vacuum pump 410 is used to evacuate vacuum vessel 400 to a pressure of, for example, $10^{-6}$ torr. Ion gun 130 is used to perform ion beam etching of the surface 2 to be prepared, as described elsewhere herein. Process gas suitable for RIE, such as $CF_4$, is fed into the vacuum vessel 400 by a controller (not shown) such as a mass-flow controller 140 shown in FIG. 1, and the electrodes comprising moveable plate 430 and stub-mounted specimen 3 are energized by a source of alternating voltage (not shown) to perform plasma etching of all or part of the surface 2. Vacuum pump 410 is turned off and a vent gas is admitted to vacuum vessel 400 to raise its pressure to atmospheric. Then, the specimen 1 is removed from the vacuum vessel through port 420 and transferred to the SEM for viewing. The benefits in this case include the achievement of two preparation functions with only one episode of specimen handling by the operator, continuous vacuum conditions between the preparation steps, and the possibility of computer control of the processing components, including ion gun 130, specimen stage 35, vacuum pump 410, and RIE electrodes, to minimize the need for operator attention through multiple sample-preparation steps.

Figure 5:
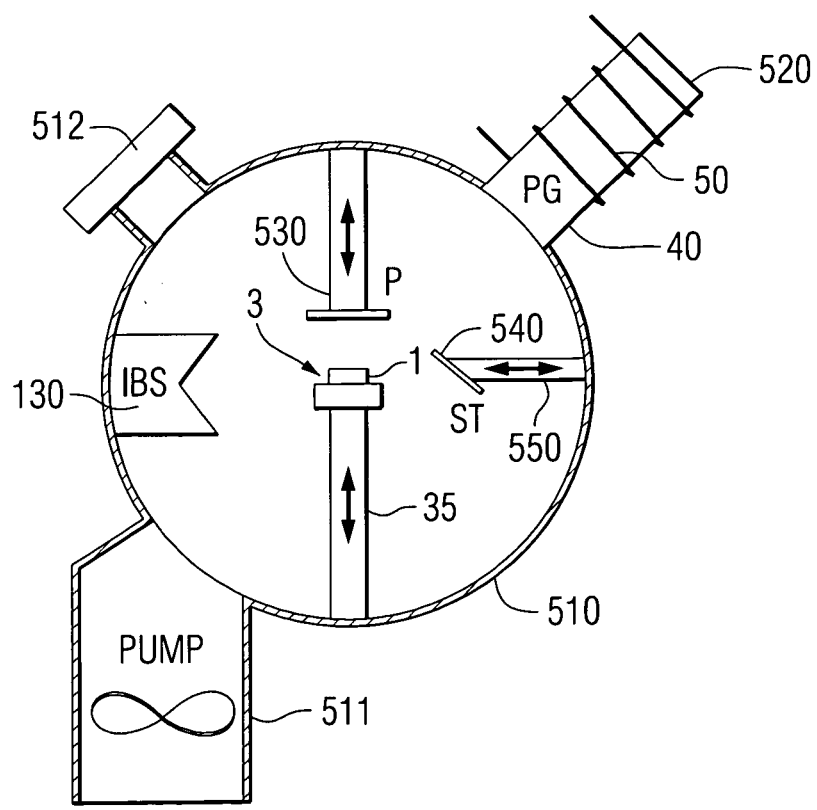
FIG. 5 is a schematic diagram of a third embodiment of an apparatus for preparing specimens for microscopy according to the present invention.

In another embodiment of the present invention, shown schematically in FIG. 5, the apparatus includes one vacuum vessel 510 having a vacuum pump 511 generally similar to vacuum pump 410 of FIG. 4, a port 512 for inserting and extracting specimens 1, a specimen stage 35 for holding and manipulating specimens 1, a plasma generator 520 for plasma cleaning, an ion gun 130 for ion beam etching, a moveable electrode 530 for performing RIE, and a sputter target 540 working in combination with ion gun 130 for depositing conductive coatings by an ion beam sputtering process. Many types of vacuum pumps are known and may be used for vacuum pump 511, such as oil diffusion pumps, turbomolecular pumps, or turbo-drag pumps. An oil-free system is preferred for minimizing the potential of contamination of the specimen 1 by hydrocarbons from the vacuum pump 511. Many types of ports are known and may be used as port 512, such as conflat flanges, ISO "KF" flanges, gate valves, or load-locks. A load-lock is preferred for rapid recovery of the vacuum after a specimen 1 is inserted. Load-locks are well known and are found, for example, in virtually all transmission electron microscopes. Many types of known plasma generators may be used for plasma generator 520 for effecting the cleaning process, but an inductively-coupled plasma generator as shown in FIGS. 1 and 5 is preferred because the flux of ions from its plasma has relatively low energy, for example 10-20 eV, and therefore is not likely to cause unintentional sputtering of the specimen 1, or thermal damage to the specimen 1. Alternative plasma generators that may be used for plasma generator 520 include capacitive-discharge plasma generators, electron-cyclotron resonance (ECR) plasma sources, and DC discharges. Many types of ion beam sources are known and may be used for ion gun 130, such as electron impact, Penning, electron beam, gaseous field ionization or Hollow-anode. Penning or Hollow-anode ion guns are preferred, because these are simple and rugged, and do not require heated filaments to produce electrons. Many types of equipment can be provided for plasma etching (RIE), such as inductively-coupled plasma generators similar to those that may be used for plasma generator 520, barrel reactors, or parallel-plate etchers. The parallel-plate geometry is preferred because, as is well known, it offers capability of etching with good material selectivity, material removal rate and directionality. Many types of equipment for depositing coatings on specimens are known such as evaporators, magnetron sputter coaters, or ion beam sputter coaters. Ion beam sputter coating using ion gun 130 and sputter target 540 is preferred because it produces fine-grain coatings and it has the potential to use the same ion beam source as is used for ion milling. In this preferred embodiment, ion gun 130 is directed toward sputter target 540, and energetic ions from the ion gun 130 collide with sputter target 540 and sputter atoms from its surface, some of which atoms impinge on specimen 1 with low velocity and adhere to its surface, resulting in a coating. In this embodiment, it is preferred that specimen stage 35 have, in addition to the ability to tilt and rotate specimens 1 as described in connection with FIG. 4, the ability to move the specimen 1 completely out of the path of the ion beam from ion gun 130. Preferably, the specimen 1 can be transposed away from the ion beam path so that the surface 2 to be prepared is situated facing the ion beam. This is to allow sputter target 540 to be inserted by way of a well-known motion mechanism 550 into the beam path, so that a separate ion gun is not needed for performing ion beam coating. The apparatus shown in FIG. 5 thus enables ion milling, plasma etching, plasma cleaning and/or coating steps to be performed in any order, any number of times, and according to various operating parameters while specimen 1 is under continuous vacuum conditions. A benefit of continuous vacuum is that it minimizes the opportunity for contamination of specimen 1 between processing steps by avoiding exposure to the atmosphere outside of vacuum vessel 510.

Figure 6:
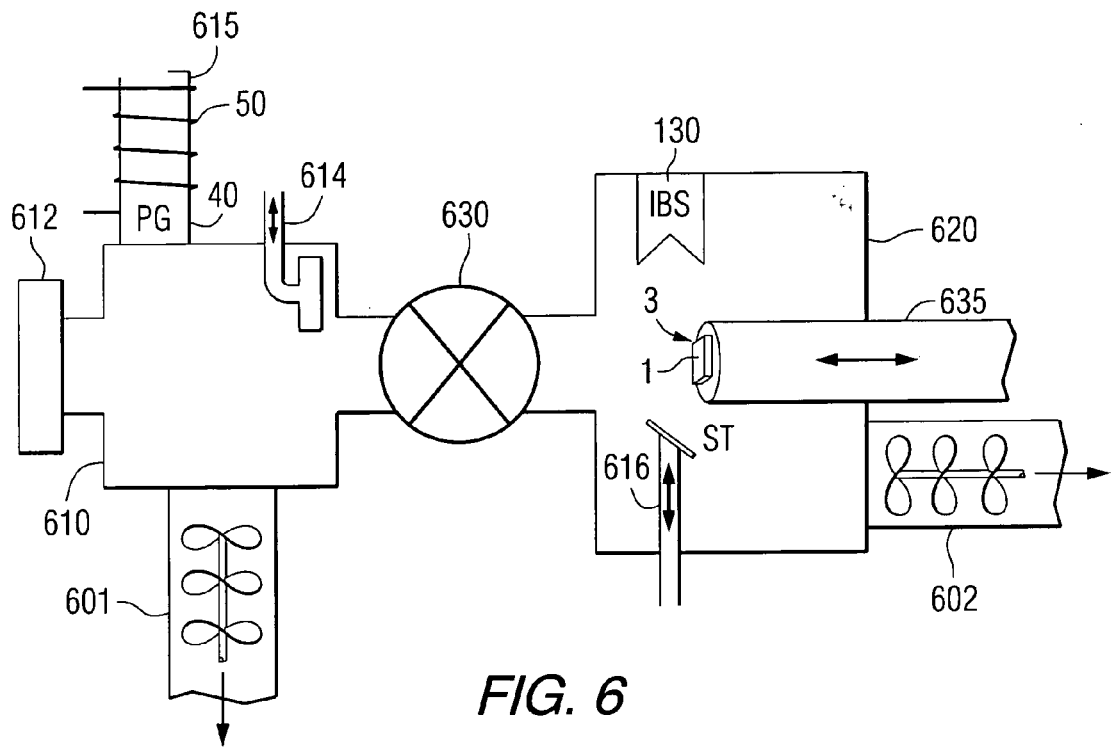
FIG. 6 is a schematic diagram of a fourth embodiment of an apparatus for preparing specimens for microscopy according to the present invention.

In still another embodiment, shown schematically in FIG. 6, the apparatus includes two vacuum vessels 610 and 620, which are joined by a shared valve 630, which valve 630 serves to isolate or connect the two vessels 610 and 620, depending on its state at a given time. Vacuum pumps 601 and 602, similar to vacuum pumps 410 and 511, are used to evacuate vessels 610 and 620, respectively to vacuum levels appropriate for their included processes. In this embodiment, the port 612 for specimen introduction and removal, the plasma generator 615, similar to plasma generator 520, and the RIE electrode 614, similar to moveable plate 430 and moveable electrode 530, are located in vessel 610, while the ion gun 130 and sputter target 616, similar to sputter target 540, are located in vessel 620. The specimen 1, or preferably stub-mounted specimen 3, is shown in FIG. 6 in position on specimen stage 635 in vessel 620. In the embodiment shown in FIG. 6, however, specimen stage 635 has the same general features and motion capabilities as specimen stage 35 of FIG. 1, except that specimen stage 635 of FIG. 6 also includes motion capability for moving the specimen 1 to various positions in either vessel 610 or vessel 620. Of course, the valve 630 must be in the open position any time specimen 1 is in vessel 610. The embodiment shown in FIG. 6 enables plasma etching and plasma cleaning steps to be performed in vessel 610, and coating and ion milling steps to be performed in vessel 620, all under continuous vacuum conditions of, for example, below 1 torr during processing and $10^{-5}$ torr between processing steps. The embodiment shown in FIG. 6 offers temporary isolation between vessels 610 and 620, which reduces the exposure of the plasma generator 615 and RIE electrode 614 to waste products from the processes of ion beam etching and/or sputter coating, which are known to produce significant quantities of waste products that can cling tenaciously to and thereby contaminate surfaces such as the walls of a vessel such as vessel 610. Specimen stage 635 and valve 630 may have mating features such that when valve 630 is open and specimen stage 635 is extended into vessel 610, specimen stage 635 and the body of valve 630 fit together, forming a more or less substantial seal against mass transfer between vessels 610 and 620. In this case, when engaged, such seal will reduce the exposure of the ion beam source 130 and sputter target 616 to waste products from the processes of plasma cleaning and/or RIE etching.

As an alternative, valve 630 may be replaced with a moveable baffle that, when closed, blocks line-of-sight travel between vessels 610 and 620. When opened, the baffle permits specimen stage 635 to move the specimen within vessel 610. The baffle has the advantage of lower cost than similarly-sized valve 630, while having the disadvantage that it permits some material to diffuse between vessels 610 and 620.

As a further alternative, plasma generator 615 or RIE electrode 614 may be moved from vessel 610 into vessel 620. As still another alternative, plasma generator 615 or RIE electrode 614 may moved from vessel 610 into vessel 620 and ion gun 130 and sputter target 616 may be moved from vessel 620 into vessel 610. Various other combinations and subcombinations of plasma generator 615, RIE electrode 614, ion gun 130 and sputter target 616 in vessels 610 and 620 are also possible.

The system shown in FIG. 6 may be further equipped with a known mechanism for handling multiple specimens 1 at one time. This offers the possibility of increased throughput of specimens through the apparatus by allowing multiple functions to occur simultaneously on different specimens 1. For example, if a load-lock is provided for introduction of the samples to the apparatus, then the load-lock may undergo initial pumping with one specimen 1 in it, while a different specimen 1 is at another station, for example plasma cleaning, in the apparatus. Such multiple-sample handling systems are well known in the industry.

Figure 7:
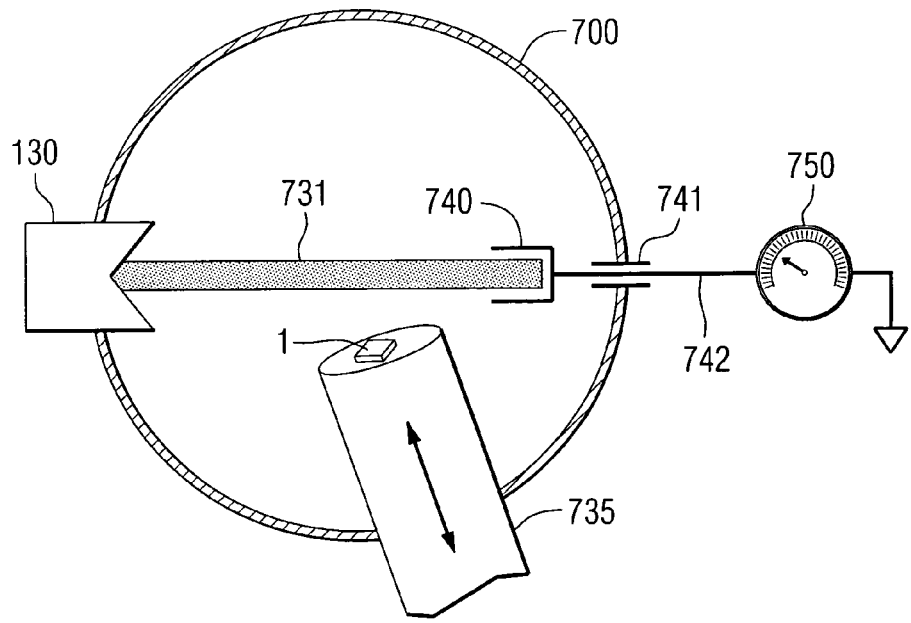
FIG. 7 is a schematic diagram of an embodiment of a system for aligning a specimen with an ion beam according to an aspect of the present invention.

One aspect of the invention, which can optionally be included in any embodiment having ion beam etching, is an adjustment for aligning the specimen with an ion beam. In prior art ion beam etchers, the sample is mounted to a manipulator such as 35 in FIG. 5, which can rotate a specimen in the plane of the surface to be prepared, such as surface 2 in FIG. 3. Generally, the manipulator's position is fixed in the direction parallel to the axis of rotation, i.e., it cannot translate in the direction perpendicular to the surface to be prepared. Because scanning electron microscope specimens can vary appreciably in height, the inability to translate in the direction perpendicular to the surface to be prepared makes alignment of the specimen and ion beam difficult. The present invention may include a specimen stage such as specimen stage 35 in FIG. 5 for translating the manipulator relative to the path of the ion beam, referred to herein as elevation. FIG. 7 shows the pertinent details of one aspect of the invention that may be used in any embodiment of the present invention having ion beam etching capabilities. In FIG. 7, a vacuum vessel 700 is shown that has the same general characteristics and components as other vacuum vessels described herein, for example vessel 510 of FIG. 5. In FIG. 7, specimen stage 735 holds specimen 1 and has various degrees of freedom of motion suitable for ion beam etching using ion gun 130, like specimen stage 35 of FIG. 1. Specimen stage 735 also has variable elevation; such variability is obtained using conventional motors, gears and the like. The present invention also includes a detection system such as Faraday cup 740 used in conjunction with ion gun 130 and current meter 750 for observing the elevation of the specimen surface to be prepared, such as surface 2 in FIG. 3. Alternately, the detection system may compromise a photodetector, such as a phototransistor, used in conjunction with an optical emitter, such as a laser diode. The detection system operates by forming a detection beam 731 between an emitter, such as ion gun 130, and a detector forming a part of the detection system described above, that is approximately parallel to the surface 2 to be prepared, so that the detection beam 731 is uninterrupted if the specimen 1 is positioned below the beam 731, and is interrupted if the specimen 1 is positioned within or above the beam 731. Ion gun 130 may be the same ion gun used in ion beam etching specimens, or may be a separate ion gun dedicated to the detection system described herein. In practice, the elevation of the specimen 1 is varied while the detection system observes whether or not the detection beam 731 is interrupted. Elevation motion may be stopped at a threshold point where the detection beam 731 is partially interrupted, thereby determining the precise location of the specimen surface to be prepared. It is preferred that this threshold location is coincident with the location of the ion etching beam, but it is also possible that the threshold location is remote from the ion etching beam, in which case a further elevation by a defined distance places the specimen's surface to be prepared within the ion etching beam. It is preferred that the operation of the detection system and specimen elevation system be under the automatic control of a computer for ease of use. Such computer control systems are well known in the art.

It will be appreciated that various elements described in detail in connection with FIG. 1 may be, where appropriate, used with or substituted into any apparatus described in FIGS. 4-7. Similarly, elements described in detail in connection with FIGS. 4-7 may be, where appropriate, used with or substituted into the apparatus described in FIG. 1.

Figure 8:
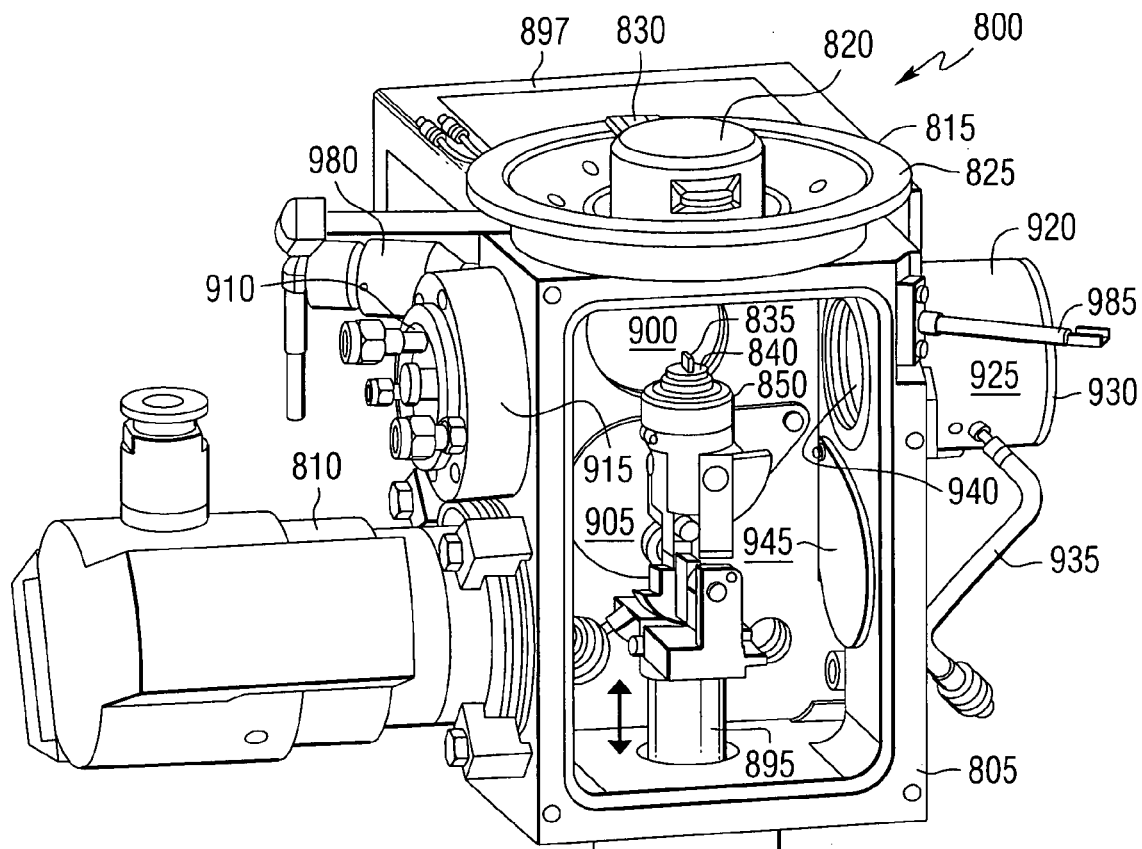
FIG. 8 is an isometric view of a fifth, preferred embodiment of an apparatus for preparing specimens for microscopy according to the present invention.
Figure 8:
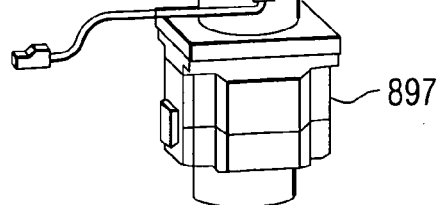

Referring to FIG. 8, a preferred embodiment of an apparatus 800 according to the present invention is shown. Apparatus 800 is shown in FIG. 8 with front door assembly 802, shown in FIG. 10, removed to enable the internal components of apparatus 800 to be seen. Apparatus 800 includes vacuum chamber 805 having turbo pump 810 similar to turbo pump 90 shown in FIG. 1 or vacuum pump 511 shown in FIG. 5. Most preferably, turbo pump 810 is an oil-free pump and is backed by an oil-free diaphragm pump (not shown). Connected to vacuum chamber 805 is load lock chamber 815 including load lock cap 820 connected to load lock bezel 825 by hinge 830. Hinge 830 allows load lock cap 820 to be lifted up and away from load lock bezel 825 by an operator when load lock chamber 815 is vented so that an operator can load specimen 835 that is mounted onto stub 840 onto moveable sample stage 850 when sample stage 850 is moved to its maximum vertical position within vacuum chamber 805. This allows vacuum chamber 805 to remain under vacuum while load lock chamber 815 is vented for specimen loading. After specimen 835 and stub 840 are loaded onto sample stage 850, load lock cap 820 may be closed, i.e., moved back into contact with load lock bezel 825, the pressure inside load lock chamber 815 may be reduced to an appropriate level, preferably on the order of $5\times10^{-5}$ torr, and processing of specimen 835 as described herein may begin.

Figure 9:
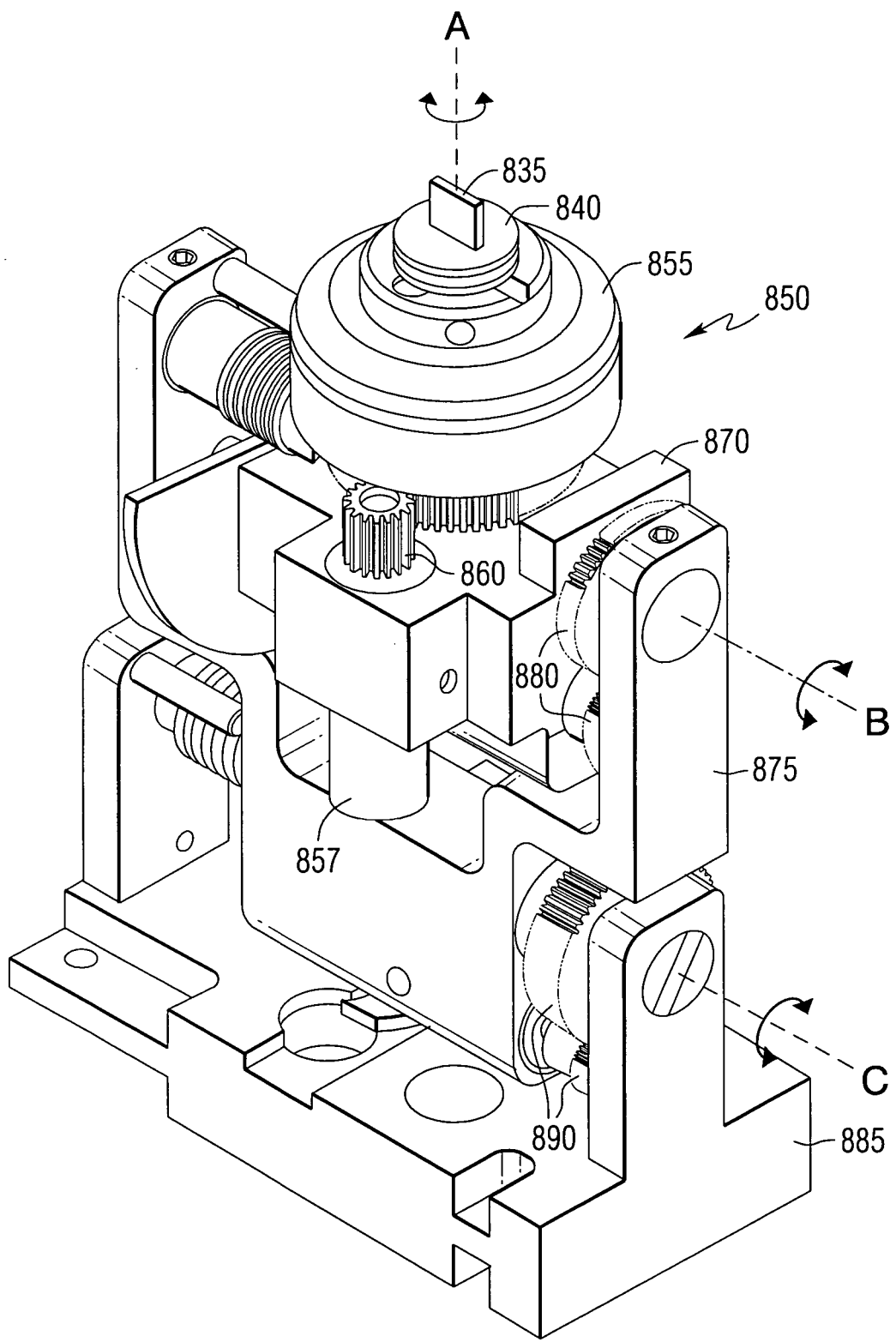
FIG. 9 is an isometric view of a sample stage forming a part of the apparatus of FIG. 8.

Referring to FIG. 9, an isometric view of sample stage 850 is shown. Sample stage 850 includes support assembly 855 that is adapted to receive and hold stub 840. Support assembly 855 is rotatable about vertical axis A shown in FIG. 9, by means of stepper motor 857 and coupled gears 860. Sample stage 850 also includes support block 870 connected to support assembly 855 and first tilt assembly 875 connected to support block 870. Support block 870, and thus support assembly 855, is rotatable with respect to first tilt assembly 875 about axis B shown in FIG. 9 by means of a stepper motor (not shown) and coupled gears 880. Because support assembly 855 is connected to support block 870 it is also rotatable about axis B. Connected to first tilt assembly 875 is second tilt assembly 885. First tilt assembly 875 is rotatable with respect to second tilt assembly 885 about axis C shown in FIG. 9 by means of a stepper motor (not shown) and coupled gears 890. In addition, referring to FIG. 8, sample stage 850 is attached to rod 895 and is moveable in a vertical direction within vacuum chamber 805 as shown by the arrows in FIG. 8 through the operation of stepper motor 897. Each of the stepper motors is under selective automatic control of a computer control system provided in connection with apparatus 800. Thus, as shown in FIGS. 8 and 9, sample stage 850 has the following four degrees of selective independent motion: (1) rotation about axis A; (2) rotation about axis B, referred to as tilt; (3) rotation about axis C, also referred to as tilt; and (4) vertical movement within vacuum chamber.

Figure 11:
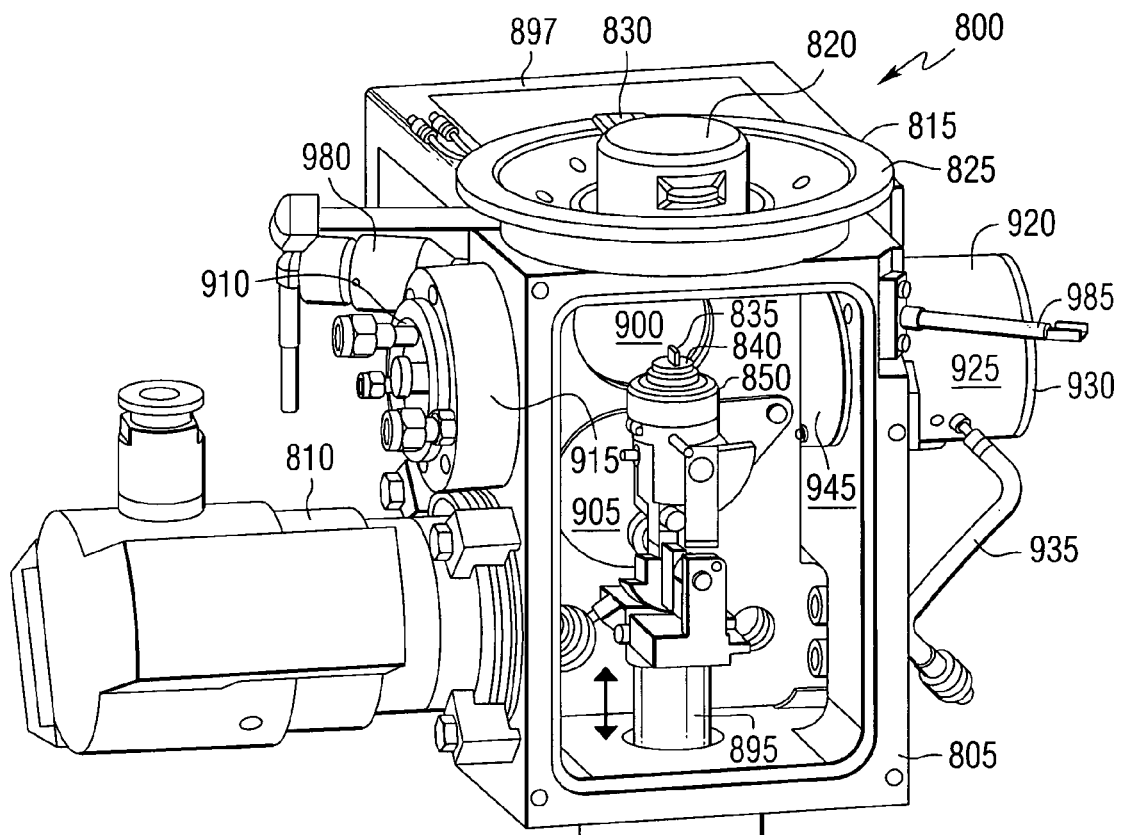
FIG. 11 is an isometric view of the apparatus of FIG. 8 wherein the specimen is positioned for plasma cleaning.
Figure 11:
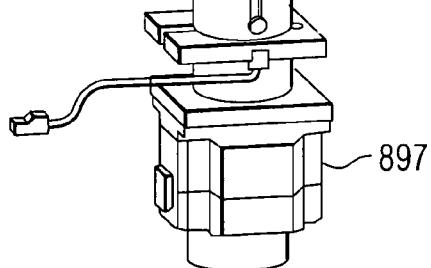

Referring again to FIG. 8, apparatus 800 further includes a plasma generator housed within shield 897 for plasma cleaning specimen 835 within vacuum chamber 805. Many types of plasma generators as described elsewhere herein may be used, but an inductively coupled plasma generator as shown in FIGS. 1 and 5 is preferred. Vacuum chamber 805 is provided with aperture 900 which allows the plasma generated by the plasma generator housed within shield 897 to flow into vacuum chamber 805 to plasma clean specimen 835. Moveable shutter 905 is provided within vacuum chamber 805 and is adapted to be moved, preferably automatically, to a position that covers aperture 900 when plasma cleaning is not being performed to protect the components of the plasma generator from contamination when the other specimen preparation processes described herein are being performed. Referring to FIG. 11, when specimen 835 is to be plasma cleaned, sample stage 850 is moved, preferably automatically, to a position as shown in FIG. 11 through operation of the appropriate stepper motors. In the position shown in FIG. 11, specimen 835 is positioned adjacent aperture 900 and shutter 905 is moved to the open position.

Figure 12:
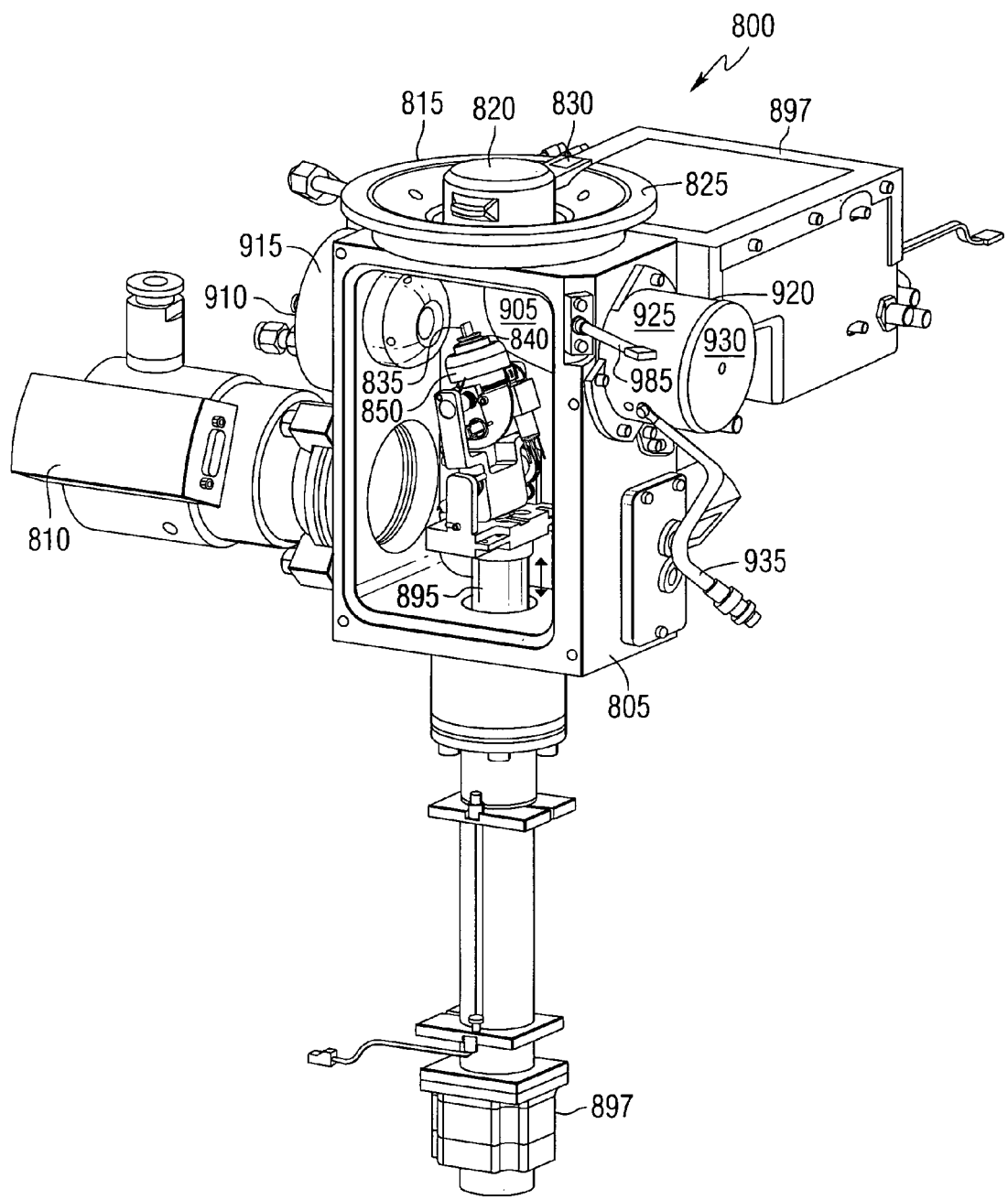
FIG. 12 is an isometric view of the apparatus of FIG. 8 wherein the specimen is positioned for etching.

As shown in FIG. 8, apparatus 800 also includes ion source 910 for ion beam etching or reactive ion beam etching specimen 835 within vacuum chamber 805. Ion source 910 is mounted within cooling flange 915 attached to vacuum chamber 805. One or more process gasses, such as an inert gas for ion beam etching and a reactive gas for reactive ion beam etching, are supplied to ion source 910 from a source (not shown) such as a compressed gas cylinder through one or more gas inlets. One or more mass flow controllers (not shown) are provided to regulate the flow of each process gas. In the preferred embodiment, apparatus 800 includes two gas inlets, each having a corresponding mass flow controller, one being for an inert gas such as argon and the other being for a reactive gas such as $CF_4$. Many types of ion sources are known and may be used for ion source 910, such as electron impact, Penning, electron beam, gaseous field ionization or Hollow-anode discharge ion sources. A Hollow-anode discharge type of ion source is preferred. Referring to FIG. 12, when specimen 835 is to be etched, sample stage 850 is moved, preferably automatically, to a position as shown in FIG. 12 through operation of the appropriate stepper motors. In the position shown in FIG. 12, specimen 835 is positioned in the ion beam generated by ion source 910, preferably in the center of the beam. In addition, through selective operation of the stepper motors, specimen 835 can be moved from a position in which the ion beam is incident on its surface at an angle of 90°, for ion milling specimen 835, to a position in which the ion beam is incident on its surface at an angle of 0°, for planarizing specimen 835, or to any position in between 0° and 90°. In addition, specimen 835 can be selectively rotated about axis A shown in FIG. 9 to assure uniform treatment of a given area as a function of time.

Figure 13:
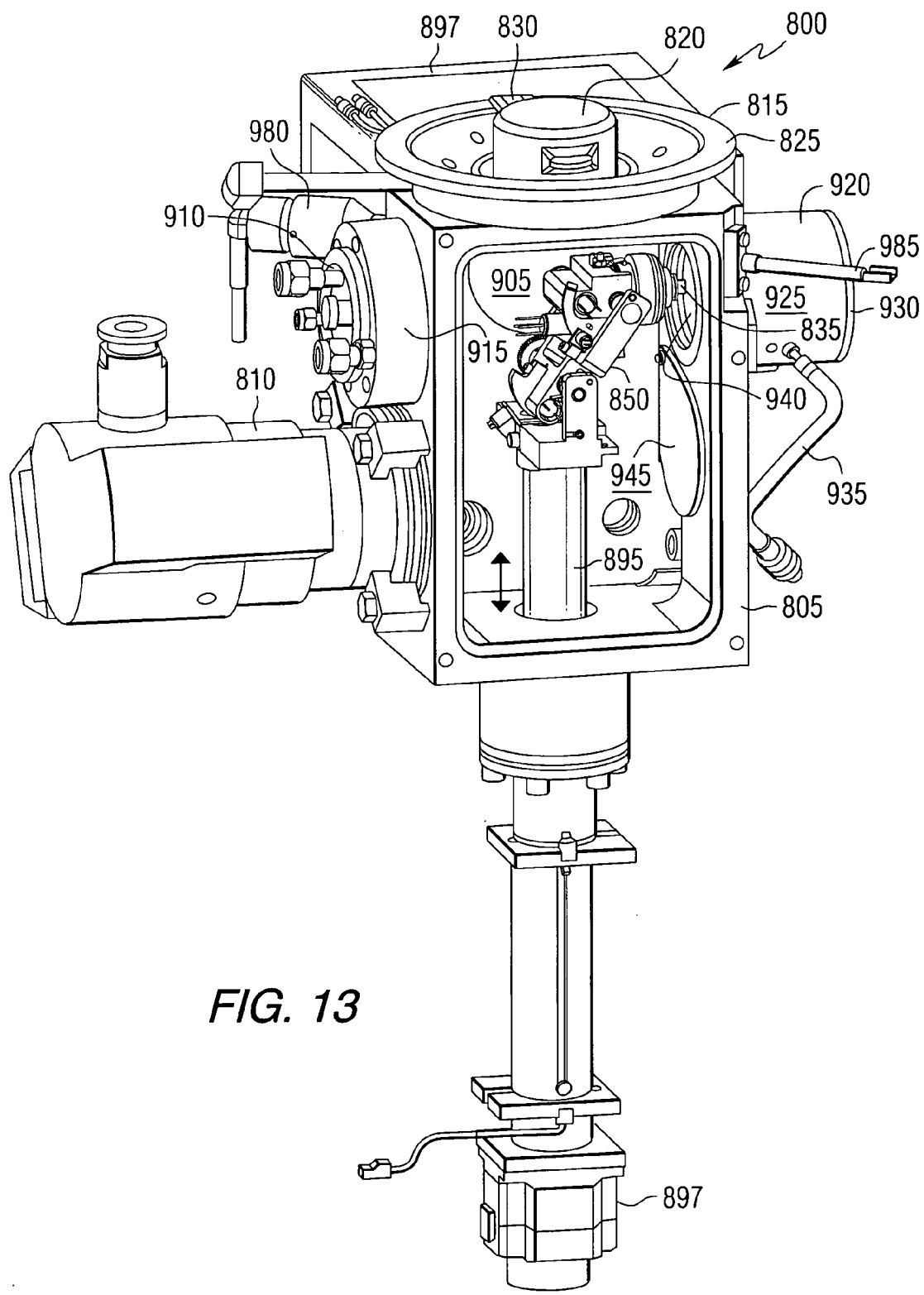
FIG. 13 is an isometric view of the apparatus of FIG. 8 wherein the specimen is positioned for plasma etching.

Apparatus 800 further includes RIE assembly 920 attached to vacuum chamber 805 for plasma etching, also known as reactive ion etching, specimen 835. In the preferred embodiment, RIE assembly 920 utilizes a plasma created by capacitive discharge techniques, described in greater detail above, in which the plasma is created between two substantially parallel electrodes. In this embodiment, RIE assembly 920 comprises vessel 925 having a plate supported therein which serves as one of the electrodes required for creation of the plasma. End cap 930 is affixed to the end of vessel 925 to seal vessel 935. An alternating RF voltage source 935 is provided and is connected to the plate supported in vessel 925 for creating the plasma inside vessel 925 from a gas that is provided thereto. In the most preferred embodiment, RIE assembly 920 is provided with multiple gas inlets, e.g., three gas inlets, to allow the plasma to be selectively created from a variety of process gasses such as $O_2$, $CF_4$ and $CHF_3$. The introduction of selected quantities and concentrations of each gas is preferably independently controlled to allow a user to custom mix or blend of gasses for specific material removal applications. Preferably, three process gasses are provided, being selected from oxidizers, reducers and non-reactive gasses. A typical gas mixture for Copper based semiconductor material is a 90% $CF_4$/10% $O_2$ mix. Such a mixture may also include some percentage of $CHF_3$, $H_2$ or various Cl based gasses. Referring to FIG. 13, when specimen 835 is to be plasma etched, sample stage 850 is moved, preferably automatically, to a position as shown in FIG. 13 through operation of the appropriate stepper motors. In the position shown in FIG. 13, specimen 835 is positioned adjacent to aperture 940 provided in vacuum chamber 805. Preferably, the surface of specimen 835 is parallel to the plate supported in vessel 925. Support assembly 855 of sample stage 850 is the second electrode used for the generation of the plasma. Moveable shutter 945 is provided in vacuum chamber 805 and is adapted to be moved, preferably automatically, to a position that covers aperture 940 when plasma etching is not being performed to protect the components of RIE assembly 920 from contamination when the other specimen preparation processes described herein are being performed. The power level of RF voltage source 935 and the distance between the plate supported in vessel 925 and the surface of specimen 835 are preferably adjustable to allow the plasma etching performance and characteristics to be changed. The distance between the plate supported in vessel 925 and the surface of specimen 835 is varied depending on how far sample stage 850 is inserted into vessel 925. These parameters are preferably automatically controlled through the computer control system provided with apparatus 800.

RIE assembly 920 may also be used to plasma clean a specimen by introducing a process gas that includes oxygen through one of the gas inlets and generating a plasma from the process gas. The process gas may also include other gases such as argon or another non-reactive gas.

Figure 10:
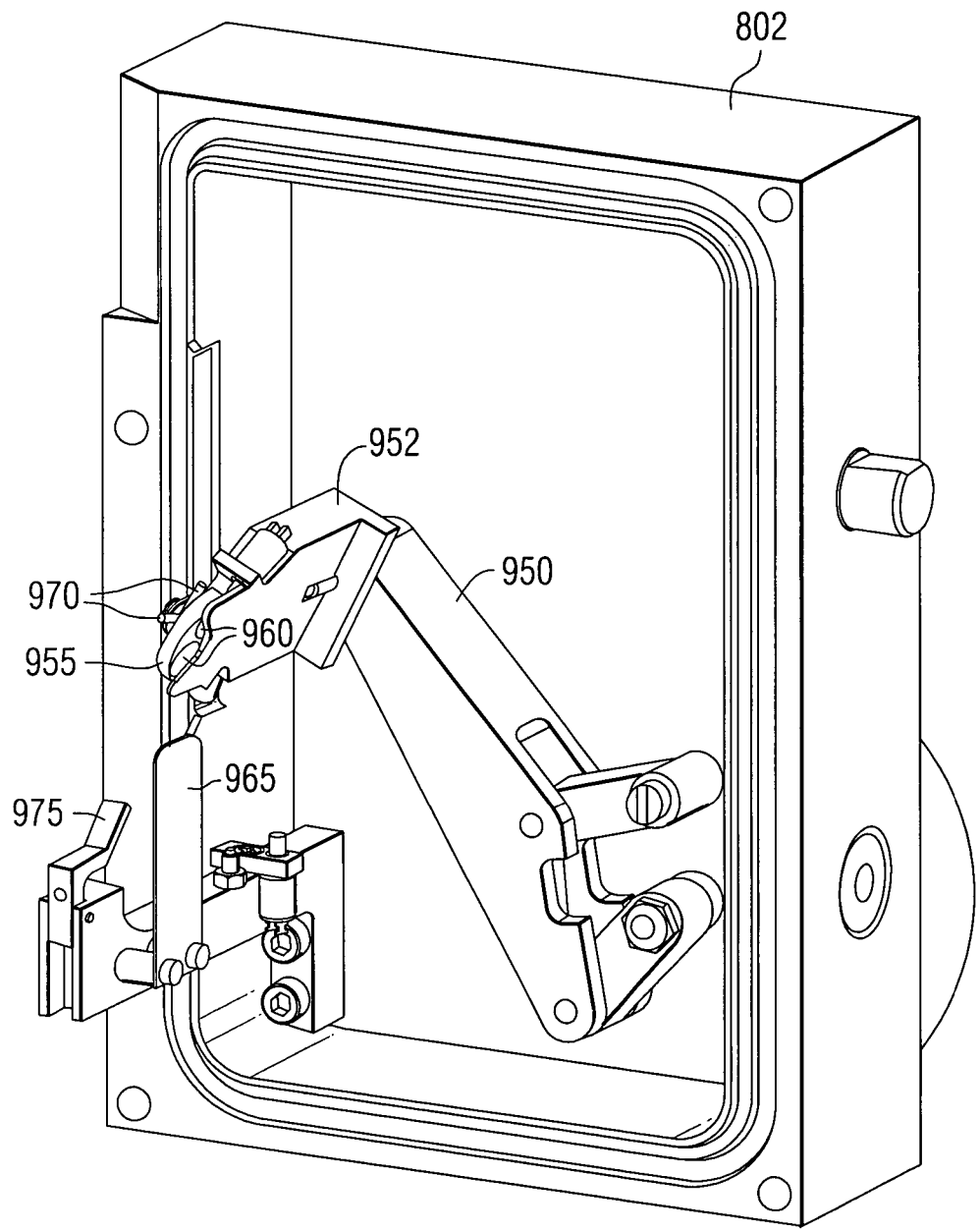
FIG. 10 is an isometric view of a front door assembly forming a part of the apparatus of FIG. 8.
Figure 14:
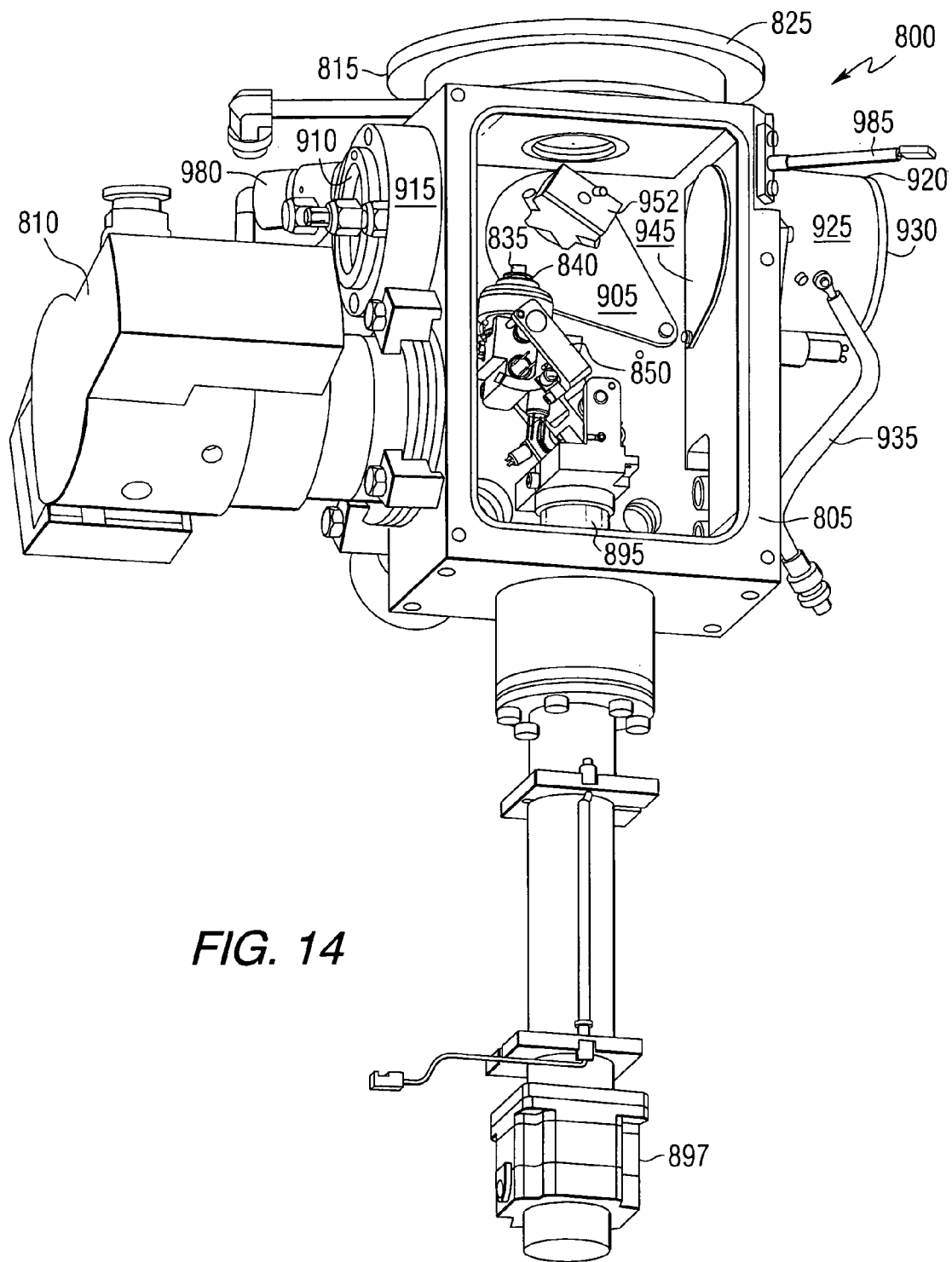
FIG. 14 is an isometric view of the apparatus of FIG. 8 wherein the specimen is positioned for coating.

Apparatus 800 is also adapted to deposit conductive coatings on specimen 835. Preferably, the coating of specimen 835 is performed using an ion beam sputtering process, described in detail elsewhere herein, in which ion source 910 works in combination with a sputter target. Specifically, referring to FIG. 10, front door assembly 802 is adapted to be attached to the front of vacuum chamber 805 and includes lever 950 having target support head 952 that supports target holder 955. Target holder 955 holds one or more targets 960 used for ion beam sputter coating of specimen 835. Lever 950 is moveable between a first position (not shown in FIG. 10) in which target holder 955 is hidden behind target shield 965, to protect targets 960 when not in use, and a second position (also not shown in FIG. 10) in which the selected target 960 is in line with the ion beam generated by ion source 910. FIG. 10 illustrates an interim position between these two positions. Referring to FIG. 14, when ion beam sputter coating of specimen is to be performed, sample stage 850 is moved, preferably automatically, to a position as shown in FIG. 14 in which specimen 835 is outside of the ion beam generated by ion source 910. Preferably, specimen 835 is moved to a position roughly one half inch away from the selected target 960 and begins the coating sequence parallel to the selected target 960. During coating, specimen 835 is preferably tilted about the top surface thereof as described below. Lever arm 950 is moved, preferably automatically, to a position in which the selected target 960 intersects the axis of the ion beam generated by ion source 910 (only target support head 952 is shown in FIG. 14 for illustrative purposes). In this position, the ion beam bombards target 960 and sputters atoms from the surface of target 960, which atoms rain down onto specimen 835 and adhere to its surface, resulting in the coating of the surface. Through selective, and preferably automatic, operation of the stepper motors that control sample stage 850, specimen 835 may be rotated about axis A shown in FIG. 9 and tilted about the top of the surface of specimen 835, also known as rocking, to provide for uniform coating of the surface of specimen 835. This tilting is effected by the selective rotation about axes B and C shown in FIG. 9 and the selective vertical movement of sample stage 850 as shown by the arrows in FIG. 8.

Figure 15:
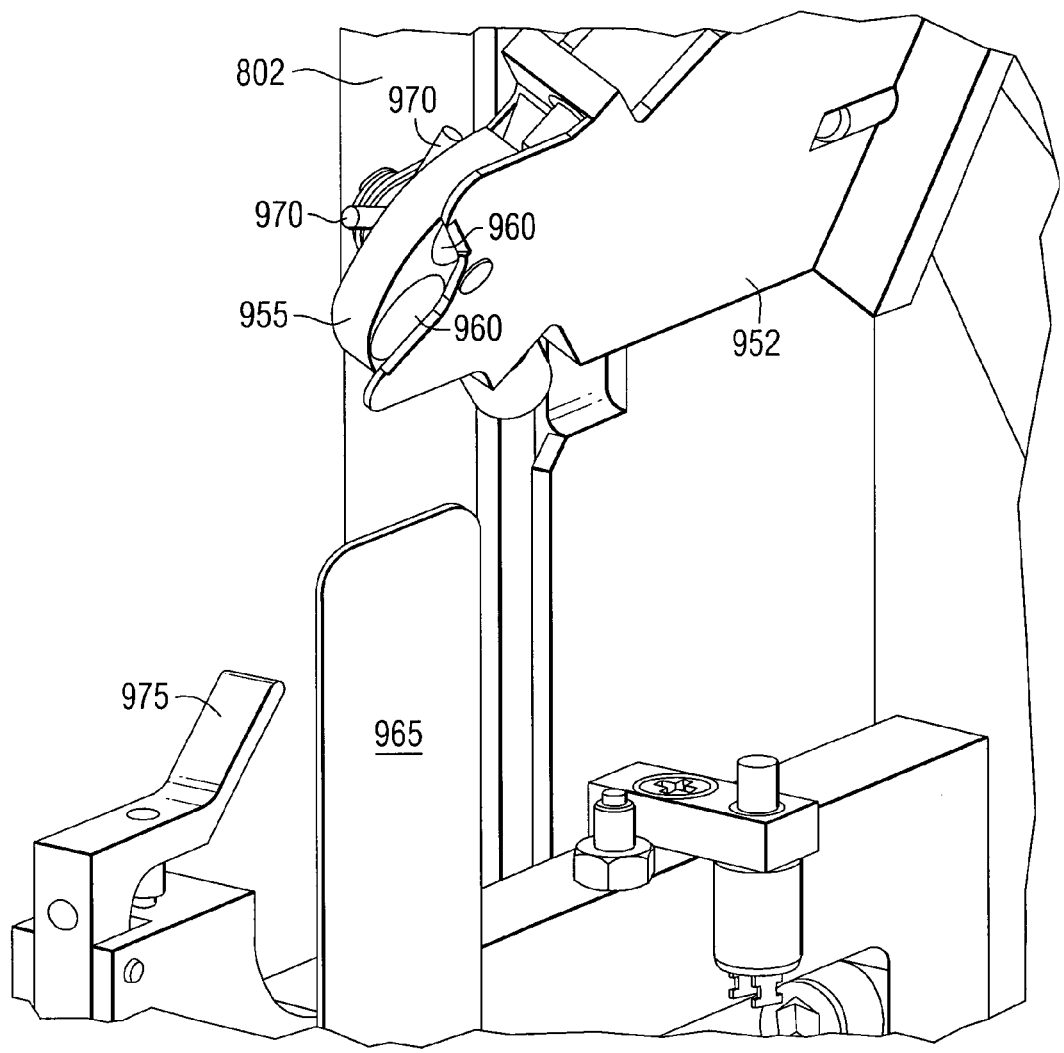
FIG. 15 is a partial isometric view of the front door assembly shown in FIG. 10.

In the most preferred embodiment, apparatus 800 includes a mechanism for housing single or multiple targets 960, such as targets made of different materials, and selectively utilizing specific ones of the targets 960 during the coating process. Specifically, as shown in FIG. 10 and also in FIG. 15, target holder 955 is disc shaped and holds multiple targets 960. Target holder 955 is adapted to rotate within target support head 952 among a number of positions. In each rotation position, a selected one of targets 960 is exposed while the remaining targets 960 are hidden behind a portion of target support head 952. Target holder 955 includes pins 970 extending therefrom. Target holder 955 is rotated among the various rotation positions through the cooperation of pins 970 and arm 975 provided on front door assembly 802. In particular, to rotate target holder 955 from one position to the next, lever 950 is first lifted upwardly from its first position in which target holder 955 is hidden behind target shield 965 and then dropped back down to such first position. During this sequence of movements, specifically on the downward movement, one of pins 970 will contact arm 975 and cause target holder 955 to rotate one position. This process may be repeated as many times as is necessary to move a desired target 960 in the position in which it is exposed. The automatic control of apparatus 800 is preferably adapted to automatically track the position of each particular target 960 so that each can selectively and, preferably automatically, be moved into position for use in coating specimen 835.

According to a most preferred embodiment, apparatus 800 further includes a system for detecting a height position of the surface of specimen 835 along a vertical axis of the interior of vacuum chamber 805. This vertical axis is parallel to the longitudinal axis of rod 895 shown in FIG. 8 and the vertical axis of movement of rod 895 shown by the arrows in FIG. 8. The determination of this height position is important because once it is determined, apparatus 800 is able to automatically move sample stage 850 to the appropriate processing positions shown in FIGS. 11-14, where specimen 835 is properly positioned for processing, through operation of the various stepper motors. The calculations required for these movements and the automatic operation of the stepper motors are based on this initial height position along the vertical axis. In particular, the height position is measured relative to a fixed position along the vertical axis, for example the position of the top of sample stage 850 without specimen 835 or stub 840. For each new specimen 835 to be processed, all that needs to be determined for automatic positioning and processing to be possible is this relative height position. Once measured, the relative height position is then utilized in the calculations and algorithms used for controlling the stepper motors and moving sample stage 850 as required, which calculations and algorithms do not change from specimen to specimen. The development of the specific algorithms required for this automatic positioning is within the ordinary skill of the art and will not be described in detail herein.

As shown in FIG. 8, according to the most preferred embodiment of apparatus 800, a laser 980 sensor 985 are provided to detect the height position of the surface of specimen 835. A suitable example of laser 980 is the part #0221-015-00 laser sold by Coherent Inc., which is a 1 mW, 670 nm wavelength laser. A suitable example of sensor 985 is part #11-01-006 optical sensor from UDT Sensors Inc. tuned for the 670 nm wavelength. A ion source may be used as an alternative to laser 980 and a Faraday cup may be used as an alternative to sensor 985.

Figure 16:
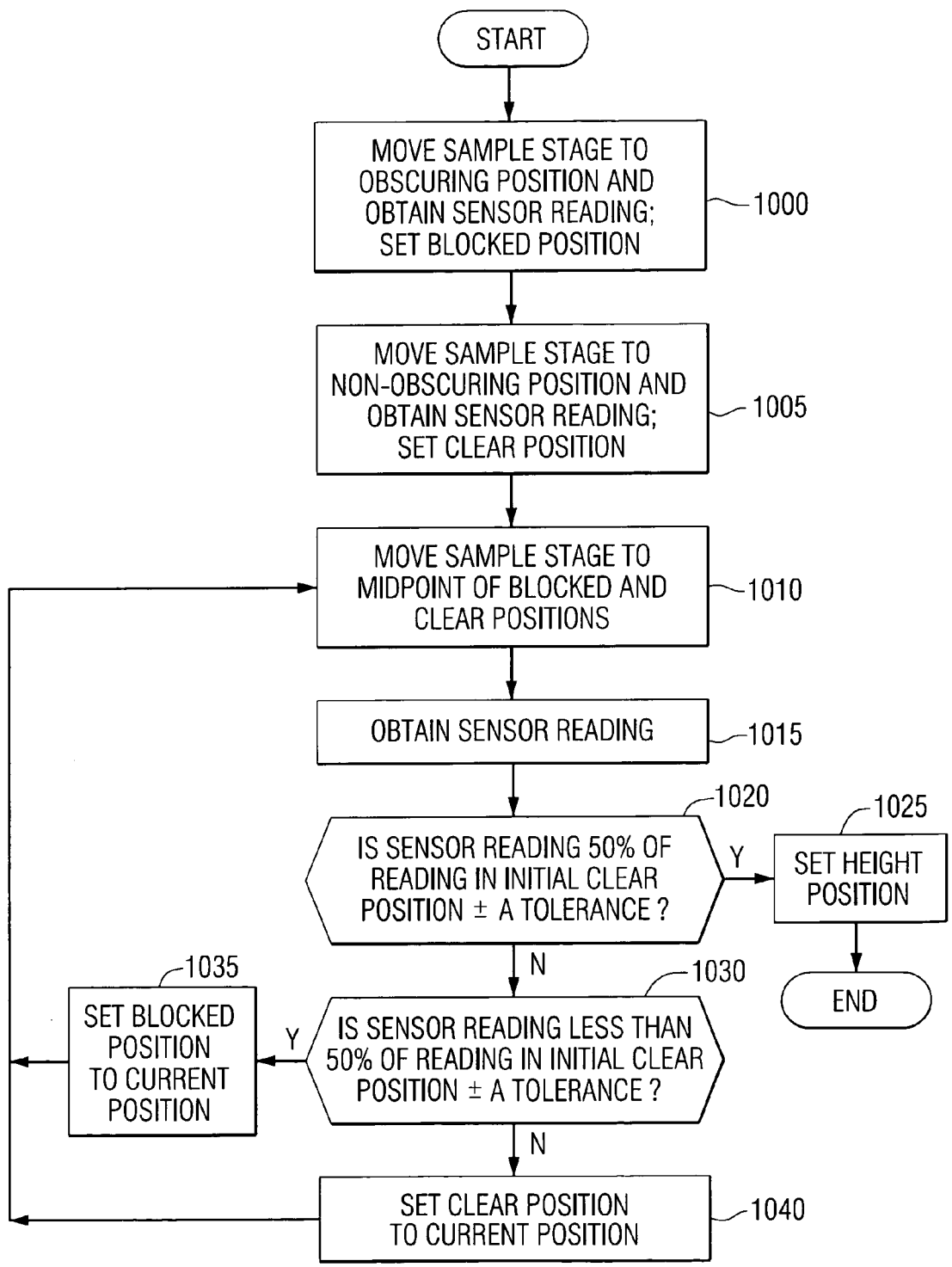
FIG. 16 is a flow diagram illustrating a method for detecting a height position of a surface of a specimen according to an aspect of the present invention.

Laser 980 is positioned such that the laser beam it generates is received by sensor 985 when the path of the laser beam is not obscured by sample stage 850. The height position of the surface of specimen 835 as described herein may thus be determined by moving sample stage 850 to a vertical position that completely obscures the laser beam, i.e., where sensor 985 is covered, and moving sample stage 850 downwardly until sensor 985 senses a predetermined intensity level of the laser beam. FIG. 16 is a flow chart that illustrates the presently preferred method for determining the height position of the surface of specimen 835. Referring to block 1000, sample stage 850 is first moved to a position in which the laser beam is completely obscured, i.e., where no level is sensed by sensor 985, and a reading from sensor 985 is obtained. A variable known as blocked position is then set to equal the current vertical position of sample stage 850. Next, as shown in block 1005, sample stage 850 is then moved to a vertical position in which the laser beam is completely unobscured and a reading from sensor 985 is obtained. A variable known as clear position is then set to the then current position of sample stage 850. Next, referring to block 1010, sample stage 850 is moved to a midpoint of the blocked position and the clear position. A reading from sensor 985 is then obtained as shown in block 1015. Referring to block 1020, a determination is then made as to whether the sensor reading is at a level that is 50% of the reading obtained in the initial clear position plus or minus some preset tolerance. If the sensor reading is 50% of the reading in the initial clear position plus or minus the tolerance, then, as shown in step 1025, the height position of the surface of the specimen 835 is set to the current position of sample stage 850. If the sensor reading obtained in step 1015 is not equal to 50% of the reading obtained in the initial clear position plus or minus the tolerance, then, as shown in block 1030, a determination is made as to whether the sensor reading is less than 50% of the reading obtained in the initial clear position plus or minus the tolerance. If it is, then, as shown in block 1035, the blocked position variable is set to equal the current position of sample stage 850 and the method returns to step 1010. If instead it is determined in block 1030 that the sensor reading is greater than 50% of the reading obtained in the initial clear position, then, as shown in block 1040, the clear position variable is set to the current position of sample stage 850 and the method returns to block 1010. Processing continues until the height position is set in block 1025.

Alternative mechanisms for detecting the height position of the surface of specimen 835 may also be used, including, but not limited to, mechanisms that utilize proximity sensors (Hall effect), electrical contacts, or mechanical contact switches.

The terms and expressions which have been employed herein are used as terms of description and not as limitation, and there is no intention in the use of such terms and expressions of excluding equivalents of the features shown and described or portions thereof, it being recognized that various modifications are possible within the scope of the invention claimed. Although particular embodiments of the present invention have been illustrated in the foregoing detailed description, it is to be further understood that the present invention is not to be limited to just the embodiments disclosed, but that they are capable of numerous rearrangements, modifications and substitutions.

What is claimed is:

1. An apparatus for preparing a specimen for microscopy, comprising:
    a plasma generator for plasma cleaning said specimen;
    means for removing material from said specimen;
    means for coating said specimen with a conductive material; and
    means for plasma etching said specimen which includes the selective spatial isolation of said means for plasma etching said specimen and said specimen from said plasma generator, said means for removing material and said means for coating said specimen when said means for plasma etching said specimen is operational;
    wherein said plasma cleaning of said specimen and said coating of said specimen may be performed in a single process chamber under continuous vacuum conditions.

2. An apparatus according to claim 1, wherein said means for removing comprises means for etching said specimen using an ion beam.

3. An apparatus according to claim 2, wherein said means for etching comprises an ion source for directing said ion beam at said specimen.

4. An apparatus according to claim 3, wherein said means for etching further comprises a source of process gas positioned adjacent said ion source.

5. An apparatus according to claim 1, said means for coating comprising a magnetron sputtering device.

6. An apparatus according to claim 1, said means for coating comprising an ion source for directing an ion beam at a target, said target being formed of said conductive material.

7. An apparatus according to claim 1, wherein said plasma generator comprises a plasma tube, a coil wrapped around said plasma tube, and an RF power supply connected to said coil.

8. An apparatus according to claim 7, further comprising a source of process gas including oxygen connected to said plasma tube, said plasma cleaning being performed using said process gas.

9. An apparatus according to claim 8, said process gas further including argon.

10. An apparatus according to claim 9, said process gas comprising a mixture of 75% argon and 25% oxygen.

11. An apparatus according to claim 8, said process gas further including a non-reactive gas.

12. An apparatus according to claim 1, further comprising a vacuum pump connected to said process chamber for evacuating said process chamber to a selected vacuum level.

13. An apparatus according to claim 12, further comprising an oil-free vacuum pump for controlling said vacuum conditions.

14. An apparatus according to claim 13, said oil-free vacuum pump selected from the group consisting of oil-free diaphragm pumps, molecular drag pumps, turbomolecular drag pumps, molecular drag pumps backed by a diaphragm pump, turbomolecular drag pumps backed by a diaphragm pump, cryosorption pumps, reciprocating piston pumps, scroll pumps, screw pumps, claw pumps, non-oil sealed single and multistage piston pumps, and rotary lobe pumps.

15. An apparatus according to claim 1, further comprising a specimen stage for holding said specimen, said specimen stage being adapted to tilt said specimen with respect to said means for removing, said specimen stage being rotatable about an axis of rotation generally perpendicular to a plane defined by a surface of said specimen when said specimen is held by said specimen stage.

16. An apparatus according to claim 15, further comprising means for cooling said specimen stage.

17. An apparatus according to claim 15, said specimen stage being selectively moveable along said axis of rotation.

18. An apparatus according to claim 1, said chamber further comprising a specimen stage for holding said specimen, said specimen stage being adapted to tilt said specimen with respect to said means for removing, said specimen stage being rotatable about an axis of rotation generally perpendicular to a plane defined by a surface of said specimen when said specimen is held by said specimen stage.

19. An apparatus according to claim 1, said chamber further comprising a cold trap.

20. An apparatus according to claim 1, said chamber further comprising a crystal oscillator for measuring an amount of said conductive material that is deposited on said specimen.

21. An apparatus according to claim 1, said plasma etching further comprising capacitive discharge plasma etching.

22. An apparatus according to claim 21, said means for plasma etching comprising a first electrode supported by said process chamber and a second electrode supported by said process chamber, said first and second electrodes defining a gap therebetween for receiving said specimen.

23. An apparatus according to claim 22, said first and second electrodes each comprising a substantially planar electrode, said first electrode and said second electrode being substantially parallel to one another.

24. An apparatus according to claim 23, further comprising a specimen stage for holding said specimen, said specimen stage being supported by said process chamber, at least a portion of said specimen stage being said first electrode.

25. An apparatus according to claim 24, said specimen stage being moveable in a direction substantially perpendicular to a planar surface of said first electrode.

26. An apparatus according to claim 24, said second electrode being moveable in a direction substantially perpendicular to a planar surface of said second electrode.

27. An apparatus according to claim 22, further comprising an alternating voltage source connected to said first and second electrodes for generating an electric field within said gap, said electric field generating a plasma from a gas introduced into said gap.

28. An apparatus according to claim 1, said plasma etching further comprising inductively coupled plasma etching.

29. An apparatus according to claim 2, further comprising means for ion beam etching said specimen, wherein said ion beam etching may be performed under said continuous vacuum conditions.

30. An apparatus according to claim 29, further comprising an ion source for directing an ion beam at said specimen, said ion beam etching said specimen, wherein said etching of said specimen with said ion beam may be performed under continuous vacuum conditions.

31. An apparatus according to claim 30, wherein said ion source may selectively direct said ion beam at said specimen for ion beam etching said specimen under said continuous vacuum conditions.

32. An apparatus according to claim 31, further comprising a specimen stage for holding said specimen, said specimen stage being moveable between a first position in which said specimen is within a path of said ion beam such that said ion beam is directed at and impinges upon said specimen and a second position in which said specimen is outside of said path such that said ion beam is directed at and impinges upon said target.

33. An apparatus according to claim 32, said specimen stage being adapted to tilt said specimen with respect to said ion source, said specimen stage being rotatable about an axis of rotation generally perpendicular to a plane defined by a surface at said specimen when said specimen is held by said specimen stage.

34. An apparatus according to claim 1, further comprising a load lock chamber connected to said process chamber.

35. An apparatus according to claim 29, said etching comprising reactive ion beam etching, said apparatus further comprising a source of reactive process gas connected to said ion source.

36. An apparatus according to claim 21, said plasma etching utilizing a plasma generated by capacitive discharge, said plasma etching assembly further comprising an electrode and an alternating voltage source connected to said electrode.

37. An apparatus according to claim 22, wherein one or more of a size of said gap and a power of said alternating voltage source are automatically controlled based on parameters set by a user.

38. An apparatus according to claim 37, said plasma etching assembly further comprising two or more gas inlets, said process gas comprising a mixture of two or more process gasses selected by a user.

39. An apparatus according to claim 38, wherein said process gasses further comprise at least one of $O_2$, $CF_4$ and $CHF_3$.

40. An apparatus according to claim 1, said means for plasma etching further comprising two or more gas inlets, said plasma etching of said specimen utilizing a plasma generated from a mixture of two or more process gasses selected by a user.

41. An apparatus according to claim 1, said means for plasma etching being usable to plasma clean said specimen by generating a plasma from a process gas including oxygen.

42. An apparatus according to claim 1, wherein coating comprises ion beam sputter coating, said means for coating comprising a target formed of said conductive material, said ion source directing said ion beam at said target.

43. An apparatus according to claim 42, said means for coating further comprising a lever supported by said vacuum chamber, said lever holding said target, said lever being selectively moveable into a position in which said ion beam is directed at said target.

44. An apparatus according to claim 1, said means for coating comprising a plurality of targets, each of said targets being formed of a conductive material, said ion source directing said ion beam at a selected one of said targets.

45. An apparatus according to claim 44, said means for coating further comprising means for moving said selected one of said targets from a covered position to an exposed position.

46. An apparatus according to claim 44, said means for coating further comprising a lever supported by said vacuum chamber, said lever holding said plurality of targets, said lever being selectively moveable into a position in which said ion beam is directed at said selected one of said targets.

47. An apparatus according to claim 46, said plurality of targets being held by a target holder, said target holder being moveable among a plurality of positions, each of said positions exposing one of said targets and covering a remaining one or more of said targets.

48. An apparatus according to claim 47, said target holder being rotatably supported by said lever, said target holder being rotatable among said plurality of positions.

49. An apparatus according to claim 48, said target holder further comprising a plurality of pins, said vacuum chamber supporting an arm, said target holder being selectively rotated by contact between said arm and any one of said pins.

50. An apparatus according to claim 46, further comprising means for selectively exposing said selected one of said targets and covering a remaining one or more of said targets.

51. An apparatus according to claim 1, further comprising a sample stage being moveable to a plurality of processing positions inside said vacuum chamber under said continuous vacuum conditions for performing said removing, said plasma cleaning, said plasma etching and said coating of said specimen.

52. An apparatus according to claim 51, said sample stage being automatically moveable among said processing positions based on parameters set by a user.

53. An apparatus according to claim 52, said parameters including an order of movement among selected ones of said processing positions.

54. An apparatus according to claim 51, said sample stage being moveable in a first direction along a vertical axis of said vacuum chamber, said apparatus further comprising means for detecting a first position of a surface of said specimen along said vertical axis, wherein said sample stage is moved automatically to said plurality of processing positions based on said first position.

55. An apparatus according to claim 54, wherein said first position is measured relative to a second position along said vertical axis.

56. An apparatus according to claim 51, said sample stage being moveable in a first direction along a vertical axis of said vacuum chamber, said apparatus further comprising a beam generating device and a beam sensor supported by said vacuum chamber, said beam generating device and said beam sensor being used to detect a first position of a surface of said specimen along said vertical axis, wherein said sample stage is moved automatically to said plurality of processing positions based on said first position.

57. An apparatus according to claim 56, wherein said first position is measured relative to a second portion along said vertical axis.

58. An apparatus according to claim 56, said beam generating device comprising a laser.

59. An apparatus according to claim 51, said sample stage being moveable in a first direction along a vertical axis of said vacuum chamber, at least a first portion of said sample stage that supports said specimen being rotatable about said vertical axis, and at least a second portion of said sample stage connected to said first portion being moveable in a first angular direction with respect to said vertical axis.

60. An apparatus according to claim 59, at least a third portion of said sample stage connected to said second portion being moveable in a second angular direction with respect to said vertical axis.

61. An apparatus according to claim 51, said sample stage having at least three degrees of selective independent movement.

62. An apparatus according to claim 61, sample stage having at least four degrees of selective independent movement.

63. An apparatus according to claim 1, said process chamber having a first aperture adjacent said plasma generator, a first moveable shutter for selectively covering said first aperture, a second aperture adjacent said means for plasma etching, and a second moveable shutter for selectively covering said second aperture.

* * * * *